United States Patent
Huey et al.

(10) Patent No.: US 9,737,334 B2
(45) Date of Patent: Aug. 22, 2017

(54) METHODS AND DEVICES FOR ACCESSING A BODY CAVITY

(75) Inventors: Kevin M. Huey, Cincinnati, OH (US); Matthew D. Holcomb, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 947 days.

(21) Appl. No.: 12/766,086

(22) Filed: Apr. 23, 2010

(65) Prior Publication Data

US 2010/0261975 A1 Oct. 14, 2010

Related U.S. Application Data

(63) Continuation-in-part of application No. 12/399,482, filed on Mar. 6, 2009, now abandoned, and a continuation-in-part of application No. 12/399,473, filed on Mar. 6, 2009, now abandoned.

(51) Int. Cl.
| | |
|---|---|
| *A61B 1/32* | (2006.01) |
| *A61B 17/02* | (2006.01) |
| *A61B 17/34* | (2006.01) |
| *A61B 90/00* | (2016.01) |

(52) U.S. Cl.
CPC ...... *A61B 17/3423* (2013.01); *A61B 17/3462* (2013.01); *A61B 17/3498* (2013.01); *A61B 2017/347* (2013.01); *A61B 2017/3445* (2013.01); *A61B 2017/3449* (2013.01); *A61B 2017/3464* (2013.01); *A61B 2017/3466* (2013.01); *A61B 2017/3492* (2013.01); *A61B 2090/0801* (2016.02)

(58) Field of Classification Search
USPC ....... 600/204–208, 201, 210, 215, 202, 203, 600/209, 212, 213, 216, 217
See application file for complete search history.

(56) References Cited

U.S. PATENT DOCUMENTS

| | | | |
|---|---|---|---|
| 1,777,767 | A | 10/1930 | Reid |
| 2,129,391 | A | 9/1938 | Wappler |
| 3,402,710 | A | 9/1968 | Paleschuck |
| (Continued) | | | |

FOREIGN PATENT DOCUMENTS

| | | |
|---|---|---|
| EP | 0568383 | 11/1993 |
| EP | 621009 A1 | 10/1994 |
| (Continued) | | |

OTHER PUBLICATIONS http://www.innomedic.de/en/products/innomotion_overview.php (Innomedic Products), accessed Oct. 24, 2006.

(Continued)

*Primary Examiner* — Zade Coley
(74) *Attorney, Agent, or Firm* — Mintz Levin Cohn Ferris Glovsky and Popeo, P.C.

(57) ABSTRACT

Methods and devices are provided for accessing a body cavity. In one embodiment, a surgical access device is provided that includes a housing having at least one access or sealing port for receiving a surgical instrument, and a retractor removably coupled to the housing and having a working channel configured to extend into a body cavity. The housing can include releasably matable upper and lower portions, with the upper portion being configured to freely rotate 360° relative to the lower portion and to the retractor when the housing is mated thereto.

18 Claims, 6 Drawing Sheets

(56) References Cited

U.S. PATENT DOCUMENTS

| | | | |
|---|---|---|---|
| 3,503,396 A | 3/1970 | Pierie at al. |
| 3,654,965 A | 4/1972 | Gramain |
| 3,844,272 A | 10/1974 | Banko |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,306,545 A | 12/1981 | Ivan et al. |
| 4,373,532 A | 2/1983 | Hill et al. |
| 4,402,683 A | 9/1983 | Kopman |
| 4,417,888 A | 11/1983 | Cosentino et al. |
| 4,559,947 A | 12/1985 | Renger et al. |
| 4,608,977 A | 9/1986 | Brown |
| 4,669,473 A | 6/1987 | Richards et al. |
| 4,821,719 A | 4/1989 | Fogarty |
| 4,831,070 A | 5/1989 | McInally et al. |
| 4,880,015 A | 11/1989 | Nierman |
| 5,027,800 A | 7/1991 | Rowland |
| 5,141,498 A | 8/1992 | Christian |
| 5,183,471 A | 2/1993 | Wilk |
| 5,197,955 A | 3/1993 | Stephens et al. |
| 5,201,742 A | 4/1993 | Hasson |
| 5,207,213 A | 5/1993 | Auhll et al. |
| 5,209,737 A | 5/1993 | Ritchart et al. |
| 5,209,741 A | 5/1993 | Spaeth |
| 5,209,747 A | 5/1993 | Knoepfler |
| 5,242,412 A | 9/1993 | Blake, III |
| 5,269,772 A | 12/1993 | Wilk |
| 5,275,614 A | 1/1994 | Haber et al. |
| 5,308,336 A | 5/1994 | Hart et al. |
| 5,312,023 A | 5/1994 | Green et al. |
| 5,330,437 A | 7/1994 | Durman |
| 5,330,502 A | 7/1994 | Hassler et al. |
| 5,342,396 A | 8/1994 | Cook |
| 5,345,927 A | 9/1994 | Bonutti |
| 5,350,391 A | 9/1994 | Iacovelli |
| 5,360,428 A | 11/1994 | Hutchinson, Jr. |
| 5,362,294 A | 11/1994 | Seitzinger |
| 5,366,478 A | 11/1994 | Brinkerhoff et al. |
| 5,368,597 A | 11/1994 | Pagedas |
| 5,374,277 A | 12/1994 | Hassler |
| 5,383,888 A | 1/1995 | Zvenyatsky et al. |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,403,342 A | 4/1995 | Tovey et al. |
| 5,417,203 A | 5/1995 | Tovey et al. |
| 5,443,452 A | 8/1995 | Hart et al. |
| 5,443,484 A | 8/1995 | Kirsch et al. |
| 5,445,648 A | 8/1995 | Cook |
| 5,456,684 A | 10/1995 | Schmidt et al. |
| 5,480,410 A | 1/1996 | Cuschieri et al. |
| 5,489,256 A | 2/1996 | Adair |
| 5,489,290 A | 2/1996 | Furnish |
| 5,501,653 A | 3/1996 | Chin |
| 5,514,157 A | 5/1996 | Nicholas et al. |
| 5,520,609 A | 5/1996 | Moll et al. |
| 5,520,678 A | 5/1996 | Heckele et al. |
| 5,545,123 A | 8/1996 | Ortiz et al. |
| 5,545,179 A | 8/1996 | Williamson, IV |
| 5,547,458 A | 8/1996 | Ortiz et al. |
| 5,549,637 A | 8/1996 | Crainich |
| 5,569,205 A | 10/1996 | Hart et al. |
| 5,569,254 A | 10/1996 | Carlson et al. |
| 5,571,090 A | 11/1996 | Sherts |
| 5,582,577 A | 12/1996 | Lund et al. |
| 5,582,617 A | 12/1996 | Klieman et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,607,450 A | 3/1997 | Zvenyatsky et al. |
| 5,609,601 A | 3/1997 | Kolesa et al. |
| 5,618,294 A | 4/1997 | Aust et al. |
| 5,624,381 A | 4/1997 | Kieturakis |
| 5,626,608 A | 5/1997 | Cuny et al. |
| 5,630,831 A | 5/1997 | Lahr |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,667,527 A | 9/1997 | Cook |
| 5,672,168 A | 9/1997 | de la Torre et al. |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,700,275 A | 12/1997 | Bell et al. |
| 5,704,534 A | 1/1998 | Huitema et al. |
| 5,713,919 A | 2/1998 | Lahr |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,456 A | 4/1998 | Jones et al. |
| 5,743,851 A | 4/1998 | Moll et al. |
| 5,766,205 A | 6/1998 | Zvenyatsky et al. |
| 5,772,654 A | 6/1998 | Leyva |
| 5,782,812 A | 7/1998 | Hart et al. |
| 5,782,859 A | 7/1998 | Nicholas et al. |
| 5,792,165 A | 8/1998 | Klieman et al. |
| 5,797,959 A | 8/1998 | Castro et al. |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,827,323 A | 10/1998 | Klieman et al. |
| 5,836,960 A | 11/1998 | Kolesa et al. |
| 5,840,078 A | 11/1998 | Yerys |
| 5,853,395 A | 12/1998 | Crook et al. |
| 5,865,807 A | 2/1999 | Blake, III |
| 5,876,447 A | 3/1999 | Arnett |
| 5,880,441 A * | 3/1999 | Hartman et al. ............ 219/689 |
| 5,891,013 A | 4/1999 | Thompson |
| 5,893,878 A | 4/1999 | Pierce |
| 5,906,577 A | 5/1999 | Beane et al. |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 6,007,561 A | 12/1999 | Bourque et al. |
| 6,024,708 A | 2/2000 | Bales et al. |
| 6,024,736 A | 2/2000 | de la Torre et al. |
| 6,027,522 A | 2/2000 | Palmer |
| 6,033,428 A | 3/2000 | Sardella |
| RE36,702 E | 5/2000 | Green et al. |
| 6,074,419 A | 6/2000 | Healy et al. |
| 6,077,288 A | 6/2000 | Shimomura et al. |
| 6,086,603 A * | 7/2000 | Termin et al. ............ 606/191 |
| 6,093,141 A | 7/2000 | Mosseri et al. |
| 6,110,154 A | 8/2000 | Shimomura et al. |
| 6,110,182 A | 8/2000 | Mowlai-Ashtiani |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,149,642 A | 11/2000 | Gerhart et al. |
| 6,156,184 A | 12/2000 | Antonucci et al. |
| 6,159,200 A | 12/2000 | Verdura et al. |
| 6,162,196 A | 12/2000 | Hart et al. |
| 6,165,184 A | 12/2000 | Verdura et al. |
| 6,171,282 B1 | 1/2001 | Ragsdale |
| 6,197,034 B1 | 3/2001 | Gvozdic et al. |

(56) References Cited

U.S. PATENT DOCUMENTS

| | | |
|---|---|---|
| 6,217,555 B1 | 4/2001 | Hart et al. |
| 6,220,248 B1 | 4/2001 | Voegele et al. |
| 6,228,055 B1 | 5/2001 | Foerster et al. |
| 6,245,052 B1 | 6/2001 | Orth et al. |
| 6,254,533 B1 | 7/2001 | Fadem et al. |
| 6,258,069 B1 | 7/2001 | Carpentier et al. |
| 6,258,102 B1 | 7/2001 | Pagedas |
| 6,261,302 B1 | 7/2001 | Voegele et al. |
| 6,264,599 B1 | 7/2001 | Slater et al. |
| 6,290,705 B1 | 9/2001 | Chan et al. |
| 6,293,966 B1 | 9/2001 | Frantzen |
| 6,315,770 B1 | 11/2001 | de la Torre et al. |
| 6,319,246 B1 | 11/2001 | de la Torre et al. |
| 6,347,940 B1 | 2/2002 | Gordils Wallis et al. |
| 6,348,034 B1 | 2/2002 | Thompson |
| 6,350,236 B1 | 2/2002 | Hipps et al. |
| 6,352,503 B1 | 3/2002 | Matsui et al. |
| 6,400,979 B1 | 6/2002 | Stoianovici et al. |
| 6,425,903 B1 | 7/2002 | Voegele |
| 6,443,960 B1 | 9/2002 | Brabrand et al. |
| 6,447,443 B1 | 9/2002 | Keogh et al. |
| 6,447,489 B1 | 9/2002 | Peterson |
| 6,454,783 B1 | 9/2002 | Piskun |
| 6,458,077 B1 | 10/2002 | Boebel et al. |
| 6,471,714 B1 | 10/2002 | Kim |
| 6,485,467 B1 | 11/2002 | Crook et al. |
| 6,551,270 B1* | 4/2003 | Bimbo et al. ............... 604/93.01 |
| 6,551,282 B1 | 4/2003 | Exline et al. |
| 6,578,577 B2 | 6/2003 | Bonadio et al. |
| 6,579,304 B1 | 6/2003 | Hart et al. |
| 6,589,167 B1 | 7/2003 | Shimomura et al. |
| 6,605,063 B2 | 8/2003 | Bousquet |
| 6,613,068 B2 | 9/2003 | Ouchi et al. |
| 6,623,426 B2 | 9/2003 | Bonadio et al. |
| 6,634,883 B2 | 10/2003 | Ranalli |
| 6,663,641 B1 | 12/2003 | Kovac et al. |
| 6,665,554 B1 | 12/2003 | Charles et al. |
| 6,666,854 B1 | 12/2003 | Lange et al. |
| 6,669,674 B1 | 12/2003 | Macoviak et al. |
| 6,673,092 B1 | 1/2004 | Bacher |
| 6,706,033 B1 | 3/2004 | Martinez et al. |
| 6,706,050 B1 | 3/2004 | Giannadakis |
| 6,725,083 B1 | 4/2004 | Burbank et al. |
| 6,764,473 B2 | 7/2004 | Morton |
| 6,766,186 B1 | 7/2004 | Hoyns et al. |
| 6,807,965 B1 | 10/2004 | Hickle |
| 6,810,880 B1 | 11/2004 | Jennings, Jr. et al. |
| 6,818,007 B1 | 11/2004 | Dampney et al. |
| 6,821,247 B2 | 11/2004 | Vierra et al. |
| 6,846,287 B2 | 1/2005 | Bonadio et al. |
| 6,908,430 B2 | 6/2005 | Caldwell et al. |
| 6,936,061 B2 | 8/2005 | Sasaki |
| 6,939,296 B2 | 9/2005 | Ewers et al. |
| 6,942,671 B1* | 9/2005 | Smith ........................... 606/108 |
| 6,945,932 B1 | 9/2005 | Caldwell et al. |
| 6,966,876 B2 | 11/2005 | Irion et al. |
| 6,972,026 B1 | 12/2005 | Caldwell et al. |
| 6,994,712 B1 | 2/2006 | Fisher et al. |
| 7,008,377 B2 | 3/2006 | Beane et al. |
| 7,014,628 B2 | 3/2006 | Bousquet |
| 7,021,173 B2 | 4/2006 | Stoianovici et al. |
| 7,047,063 B2 | 5/2006 | Burbank et al. |
| 7,052,454 B2 | 5/2006 | Taylor |
| 7,083,576 B2 | 8/2006 | Zarins et al. |
| 7,083,626 B2 | 8/2006 | Hart et al. |
| 7,087,071 B2 | 8/2006 | Nicholas et al. |
| 7,093,596 B2 | 8/2006 | Muller et al. |
| 7,118,528 B1 | 10/2006 | Piskun |
| 7,121,437 B2 | 10/2006 | Kasting |
| 7,147,650 B2 | 12/2006 | Lee |
| 7,163,510 B2 | 1/2007 | Kahle et al. |
| 7,163,525 B2 | 1/2007 | Franer |
| 7,201,734 B2 | 4/2007 | Hickle |
| 7,208,005 B2 | 4/2007 | Frecker et al. |
| 7,214,185 B1 | 5/2007 | Rosney et al. |
| 7,247,154 B2 | 7/2007 | Hickle |
| 7,311,661 B2 | 12/2007 | Heinrich |
| 7,338,473 B2 | 3/2008 | Campbell et al. |
| 7,344,547 B2 | 3/2008 | Piskun |
| 7,347,862 B2 | 3/2008 | Layer |
| 7,416,533 B2 | 8/2008 | Gellman et al. |
| 7,615,005 B2 | 11/2009 | Stefanchik et al. |
| 2001/0015355 A1* | 8/2001 | Adams et al. ................. 220/258 |
| 2001/0034528 A1 | 10/2001 | Foerster et al. |
| 2001/0053510 A1 | 12/2001 | Ranalli |
| 2002/0007112 A1 | 1/2002 | Rupp et al. |
| 2002/0026201 A1 | 2/2002 | Foerster et al. |
| 2002/0103434 A1 | 8/2002 | Swanbom |
| 2002/0156432 A1 | 10/2002 | Racenet et al. |
| 2002/0173805 A1 | 11/2002 | Matsuno et al. |
| 2002/0183594 A1 | 12/2002 | Beane et al. |
| 2002/0193815 A1 | 12/2002 | Foerster et al. |
| 2003/0028179 A1 | 2/2003 | Piskun |
| 2003/0047358 A1 | 3/2003 | Bonkowski |
| 2003/0078478 A1 | 4/2003 | Bonadio et al. |
| 2003/0100814 A1 | 5/2003 | Kindlein |
| 2003/0109898 A1 | 6/2003 | Schwarz et al. |
| 2003/0113540 A1 | 6/2003 | Anderson et al. |
| 2003/0139756 A1 | 7/2003 | Brustad |
| 2003/0206860 A1 | 11/2003 | Bleyer et al. |
| 2003/0208207 A1 | 11/2003 | Layer |
| 2003/0225420 A1 | 12/2003 | Wardle |
| 2003/0229338 A1 | 12/2003 | Irion et al. |
| 2003/0236549 A1 | 12/2003 | Bonadio et al. |
| 2004/0015185 A1 | 1/2004 | Ewers et al. |
| 2004/0023161 A1 | 2/2004 | Yamaguchi et al. |
| 2004/0024304 A1 | 2/2004 | Foerster et al. |
| 2004/0068291 A1 | 4/2004 | Suzuki |
| 2004/0069828 A1* | 4/2004 | Turner .......................... 224/660 |
| 2004/0106942 A1 | 6/2004 | Taylor et al. |
| 2004/0106986 A1 | 6/2004 | Andersson et al. |
| 2004/0111060 A1 | 6/2004 | Racenet et al. |
| 2004/0138528 A1 | 7/2004 | Richter et al. |
| 2004/0147933 A1 | 7/2004 | McGovern |
| 2004/0164017 A1* | 8/2004 | Knight ........................... 210/450 |
| 2004/0167545 A1 | 8/2004 | Sadler et al. |
| 2004/0193212 A1 | 9/2004 | Taniguchi et al. |
| 2004/0195197 A1 | 10/2004 | Miceli et al. |
| 2004/0215063 A1 | 10/2004 | Bonadio et al. |
| 2004/0225323 A1 | 11/2004 | Nagase et al. |
| 2004/0230160 A1 | 11/2004 | Blanco |
| 2004/0230161 A1 | 11/2004 | Zeiner |
| 2004/0243108 A1 | 12/2004 | Suzuki |
| 2004/0254426 A1* | 12/2004 | Wenchell ...................... 600/207 |
| 2004/0260198 A1 | 12/2004 | Rothberg et al. |
| 2004/0260337 A1 | 12/2004 | Freed |
| 2005/0020884 A1 | 1/2005 | Hart et al. |
| 2005/0033312 A1 | 2/2005 | Suzuki |
| 2005/0033342 A1 | 2/2005 | Hart et al. |
| 2005/0033357 A1 | 2/2005 | Braun |
| 2005/0085842 A1 | 4/2005 | Eversull et al. |
| 2005/0107809 A1 | 5/2005 | Litscher et al. |
| 2005/0124912 A1 | 6/2005 | Griego et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1* | 10/2005 | Wenchell ...................... 606/108 |
| 2005/0228224 A1 | 10/2005 | Okada et al. |
| 2005/0267419 A1 | 12/2005 | Smith |
| 2005/0273084 A1 | 12/2005 | Hinman et al. |
| 2005/0273132 A1 | 12/2005 | Shluzas et al. |
| 2005/0277946 A1 | 12/2005 | Greenhalgh |
| 2005/0283050 A1 | 12/2005 | Gundlapalli et al. |
| 2006/0016853 A1 | 1/2006 | Racenet |
| 2006/0020241 A1 | 1/2006 | Piskun et al. |
| 2006/0020281 A1 | 1/2006 | Smith |
| 2006/0020287 A1 | 1/2006 | Lee et al. |
| 2006/0042636 A1 | 3/2006 | Nalagatla et al. |
| 2006/0071432 A1 | 4/2006 | Staudner |
| 2006/0084842 A1 | 4/2006 | Hart et al. |
| 2006/0149137 A1 | 7/2006 | Pingleton et al. |
| 2006/0212062 A1 | 9/2006 | Farascioni |

(56) References Cited

U.S. PATENT DOCUMENTS

| | | |
|---|---|---|
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0229641 A1 | 10/2006 | Gupta et al. |
| 2006/0241651 A1 | 10/2006 | Wilk |
| 2006/0241671 A1 | 10/2006 | Greenhalgh |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1* | 11/2006 | Voegele et al. ............... 606/191 |
| 2006/0247678 A1 | 11/2006 | Weisenburgh et al. |
| 2006/0258899 A1 | 11/2006 | Gill et al. |
| 2006/0259071 A1 | 11/2006 | Nicholas et al. |
| 2006/0259073 A1 | 11/2006 | Miyamoto et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1* | 4/2007 | Brustad et al. ............... 264/102 |
| 2007/0088202 A1 | 4/2007 | Albrecht et al. |
| 2007/0088277 A1 | 4/2007 | McGinley et al. |
| 2007/0106317 A1 | 5/2007 | Shelton et al. |
| 2007/0118021 A1 | 5/2007 | Pokorney |
| 2007/0151566 A1 | 7/2007 | Kahle et al. |
| 2007/0162072 A1 | 7/2007 | Nicholas et al. |
| 2007/0185453 A1 | 8/2007 | Michael et al. |
| 2007/0208312 A1 | 9/2007 | Norton et al. |
| 2007/0244358 A1 | 10/2007 | Lee |
| 2007/0250113 A1 | 10/2007 | Hegeman et al. |
| 2007/0255219 A1 | 11/2007 | Vaugh et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0065107 A1 | 3/2008 | Larkin et al. |
| 2008/0086080 A1* | 4/2008 | Mastri et al. ............... 604/95.03 |
| 2008/0119821 A1 | 5/2008 | Agnihotri et al. |
| 2008/0132765 A1 | 6/2008 | Beckman et al. |
| 2008/0147113 A1 | 6/2008 | Nobis et al. |
| 2008/0154299 A1 | 6/2008 | Livneh |
| 2008/0157018 A1 | 7/2008 | Kessell et al. |
| 2008/0183044 A1 | 7/2008 | Colleran et al. |
| 2008/0255420 A1 | 10/2008 | Lee et al. |
| 2008/0255519 A1* | 10/2008 | Piskun et al. ............... 604/174 |
| 2008/0262492 A1 | 10/2008 | Lee |
| 2008/0269727 A1 | 10/2008 | Lee |
| 2008/0294191 A1 | 11/2008 | Lee |
| 2009/0005799 A1 | 1/2009 | Franer et al. |
| 2009/0036745 A1* | 2/2009 | Bonadio et al. ............... 600/208 |
| 2009/0058209 A1* | 3/2009 | Baranowski et al. ........... 310/91 |
| 2009/0062618 A1 | 3/2009 | Drew et al. |
| 2009/0076464 A1 | 3/2009 | Gresham |
| 2009/0088792 A1 | 4/2009 | Hoell, Jr. et al. |
| 2009/0093682 A1 | 4/2009 | Izzo et al. |
| 2009/0118587 A1* | 5/2009 | Voegele et al. ............... 600/206 |
| 2009/0171147 A1 | 7/2009 | Lee et al. |
| 2009/0206129 A1 | 8/2009 | Doll et al. |
| 2009/0221966 A1 | 9/2009 | Richard |
| 2009/0227843 A1* | 9/2009 | Smith et al. ............... 600/208 |
| 2009/0287163 A1 | 11/2009 | Fischvogt et al. |
| 2009/0306658 A1 | 12/2009 | Nobis et al. |
| 2010/0081863 A1 | 4/2010 | Hess et al. |
| 2010/0081864 A1 | 4/2010 | Hess et al. |
| 2010/0081880 A1* | 4/2010 | Widenhouse et al. ........ 600/201 |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081914 A1 | 4/2010 | Waynik et al. |
| 2010/0081995 A1* | 4/2010 | Widenhouse et al. ... 604/164.08 |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2011/0024420 A1* | 2/2011 | King ............... 220/254.8 |

FOREIGN PATENT DOCUMENTS

| | | |
|---|---|---|
| EP | 0646358 | 4/1995 |
| EP | 0776231 A1 | 6/1997 |
| EP | 950376 | 10/1999 |
| EP | 0966924 A1 | 12/1999 |
| EP | 0996925 A1 | 5/2000 |
| EP | 1219251 A1 | 7/2002 |
| EP | 1219252 A1 | 7/2002 |
| EP | 1219253 A1 | 7/2002 |
| EP | 1350476 | 10/2003 |
| EP | 1731105 A1 | 12/2006 |
| FR | 2710270 | 3/1995 |
| GB | 2130889 A | 6/1984 |
| JP | 2000033089 A | 2/2000 |
| JP | 2001231786 A | 8/2001 |
| JP | 2002028163 A | 1/2002 |
| JP | 2006320750 | 11/2006 |
| WO | WO-9608208 A1 | 3/1996 |
| WO | WO-9712557 A1 | 4/1997 |
| WO | WO-9729709 A1 | 8/1997 |
| WO | WO-9735521 A1 | 10/1997 |
| WO | WO-9810712 A1 | 3/1998 |
| WO | WO-9903536 A1 | 1/1999 |
| WO | WO-0030592 A1 | 6/2000 |
| WO | WO-0032253 A1 | 6/2000 |
| WO | WO-0217810 A2 | 3/2002 |
| WO | WO-0239890 A2 | 5/2002 |
| WO | WO-0239918 A1 | 5/2002 |
| WO | WO-02058543 A2 | 8/2002 |
| WO | WO-02094133 A1 | 11/2002 |
| WO | WO-03005890 A2 | 1/2003 |
| WO | WO-03067341 A2 | 8/2003 |
| WO | WO-03077730 A2 | 9/2003 |
| WO | WO-03091839 A2 | 11/2003 |
| WO | WO-2005087112 A1 | 9/2005 |
| WO | WO-2005094432 A2 | 10/2005 |
| WO | WO-2006110733 A2 | 10/2006 |
| WO | WO-2007119232 A2 | 10/2007 |
| WO | WO-2008012787 A2 | 1/2008 |
| WO | WO-2008024502 A2 | 2/2008 |
| WO | WO-2009073577 A2 | 6/2009 |

OTHER PUBLICATIONS http://www.intuitivesurgical.com/products/index.aspx (Intuitive Surgical Products), accessed Oct. 24, 2006.

Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.

Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.

Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.

Partial European Search Report dated Jul. 5, 2010, EP App. No. 10250400.8 (7 pages).

Stoianovici, et al., "A Novel Mechanical Transmission Applied to Percutaneous Renal Access", DSC—vol. 61, Proceedings of the ASME Dynamic Systems and Control Division 1997.

U.S. Appl. No. 12/479,030, filed Jun. 5, 2009.
U.S. Appl. No. 12/479,092, filed Jun. 5, 2009.
U.S. Appl. No. 12/479,096, filed Jun. 5, 2009.
U.S. Appl. No. 12/479,293, filed Jun. 5, 2009.
U.S. Appl. No. 12/512,542, filed Jul. 30, 2009.
U.S. Appl. No. 12/512,568, filed Jul. 30, 2009.
URobitics, Brady Urological Institute, Johns Hopkins Medical

(56) References Cited

OTHER PUBLICATIONS

Institutions, "Z-Stage PAKY", date of publication unknown but no later than Oct. 26, 2006 (date of citation in U.S. Appl. No. 11/307,231).
URobotics, Brady Urological Institute, Johns Hopkins Medical Institutions, "PAKY Needle Driver," date of publication unknown but no later than Oct. 26, 2006 (date of citation in U.S. Appl. No. 11/307,231).
URobotics, Brady Urological Institute, Johns Hopkins Medical Institutions, "The RCM Robot", date of publication unknown but no later than Oct. 26, 2006 (date of citation in U.S. Appl. No. 11/307,231).
"1 Lap Disc Hand Access Device—Ref. Ld111," by Ethicon Endo-Surgery, Inc. (date unknown but no later than May 15, 2007, date of citation in U.S. Appl. No. 11/398,985; 1 page).
"Adult Cardiac Surgical Instruments," from the website of Genesee BioMedical, Inc. (date of first publication unknown; downloaded May 3, 2007; 4 pages).
"Applied GelPort Advanced Access Device," by Applied Medical Resources Corporation (Nov. 2002).
"Applied GelPort System" by Applied Medical Resources Corporation (2004).
"Bard® Bi-Directional and Kelly-Wick Tunnelers—Instructions for Use," by Bard Peripheral Vascular (Apr. 2006).
"Hand Instruments," from the website of Olympus Surgical America (date of first publication unknown; downloaded May 3, 2007; 4 pages).
"intrack XT—Low Profile Atraumatic Clamps," by Novare Surgical Systems, Inc. (2002).
"Pen Competitors," (date of first publication unknown but no later than May 15, 2007, date of citation in U.S. Appl. No. 11/398,985; 1 page).
Advanced Surgical Concepts (ASC), 510(k) TriPort Laparoscopic Access Device, Dec. 26, 2007, 8 pages.
Ashida, R. et al., "Indocyanine Green is an Ideal Dye for Endoscopic Ultrasound-Guided Fine-Needle Tattooing of Pancreatic Tumors" *Endoscopy*, 38, pp. 190-192 (2006).
Desai, M. et al., "Laprascopic and Robtoic Urology: Scarless single port transumbilical nephrectomy and pyeloplasty: first clinical report," Journal Compilation, 2008 BJU International, 101, 83-88.
Ideas for Surgery.com, "Surgeon performs single-port laparoscopic surgery," dated Dec. 1, 2007.
Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).
*Twentieth Edition—Illustrations of Surgical Instruments*, by the Kny-Scheerer Company, New York, USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338-2348, 2352, 2355, 2359, 2371, 3017, 3039-3073, 3132, 3165, 3168-3169, 3208-3209, 3219 (Jul. 1915).
U.S. Appl. No. 12/242,333, filed Sep. 30, 2008.
U.S. Appl. No. 12/242,353, filed Sep. 30, 2008.
U.S. Appl. No. 12/242,381, filed Sep. 30, 2008.
U.S. Appl. No. 12/242,711, filed Sep. 30, 2008.
U.S. Appl. No. 12/242,721, filed Sep. 30, 2008.
U.S. Appl. No. 12/242,726, filed Sep. 30, 2008.
U.S. Appl. No. 12/242,765, filed Sep. 30, 2008.
U.S. Appl. No. 12/399,473, filed Mar. 6, 2009.
U.S. Appl. No. 12/399,482, filed Mar. 6, 2009.
U.S. Appl. No. 12/399,625, filed Mar. 6, 2009.
Webpage of Novare Surgical, Inc. featuring clamps (date of first publication unknown; downloaded Feb. 23, 2004; 1 page).
European Search Report dated Nov. 4, 2010, EP App. No. 10250440.8 (10 pages).

\* cited by examiner

METHODS AND DEVICES FOR ACCESSING A BODY CAVITY

CROSS REFERENCE TO RELATED APPLICATIONS

The present application is a continuation in part of U.S. application Ser. No. 12/399,482 filed on Mar. 6, 2009 and entitled "Methods And Devices For Providing Access Into A Body Cavity" and a continuation in part of U.S. application Ser. No. 12/399,473 filed on Mar. 6, 2009 and entitled "Methods And Devices For Providing Access Into A Body Cavity," which are hereby incorporated by reference in their entireties.

FIELD OF THE INVENTION

The present invention relates to methods and devices for accessing a body cavity.

BACKGROUND OF THE INVENTION

Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through the trocar sleeve. Laparoscopic instruments (graspers, dissectors, scissors, retractors, etc.) are placed through two or more additional trocar sleeves for manipulation by the surgeon and surgical assistant(s). However, a standard (straight) cannula limits angular movement of an instrument inserted therethrough, which can prevent the instrument from being optimally positioned during surgery. Furthermore, placement of two or more standard (straight) cannulas and laparoscopic instruments next to each other creates a so-called "chopstick" effect, which describes interference between the surgeon's hands, between the surgeon's hands and the instruments, and between the instruments. This interference greatly reduces the surgeon's ability to perform a laparoscopic procedure.

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it is desirable to perform an operation utilizing only a single incision. An umbilicus is well-hidden and the thinnest and least vascularized area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. Drawbacks with entry through the umbilicus, however, are that positions of an instrument inserted through a standard (straight) cannula are limited and that the placement of two or more standard (straight) cannulas and laparoscopic instruments in the umbilicus, next to each other, creates the "chopstick" effect.

Accordingly, there is a need for improved methods and devices which allow laparoscopic procedures to be performed entirely through the umbilicus or a surgical port located elsewhere which allow adjustment of instrument position during the surgical procedure.

SUMMARY OF THE INVENTION

The present invention generally provides methods and devices for accessing a body cavity. In one embodiment, a surgical device is provided that includes a distal housing defining a working channel, and a proximal housing removably and rotatably coupled to the distal housing such that the proximal housing can freely rotate 360° relative to the distal housing. The proximal housing has at least one sealing port formed therein for receiving a surgical instrument therethrough. The at least one sealing port is configured to form at least one of a seal around the surgical instrument inserted therethrough and a channel seal configured to form a seal when no surgical instrument is inserted therethrough. A fluid tight seal can be formed between the proximal and distal housings when the proximal and distal housings are coupled together such that the proximal housing can freely rotate 360° relative to the distal housing without release of the fluid tight seal.

The proximal housing can be freely rotatable 360° relative to the distal housing in a substantially fixed plane substantially perpendicular to a longitudinal axis of the working channel. When the proximal and distal housings are not coupled together, the proximal housing can be configured to be coupled to the distal housing at any 360° rotational orientation relative to the distal housing. Similarly, when the proximal and distal housings are coupled together, the proximal housing can be configured to be removed from the distal housing at any 360° rotational orientation relative to the distal housing.

The proximal and distal housings can be removably and rotatably coupled together in any number of ways. In one exemplary embodiment, one of the proximal and distal housings can include at least one living hinge for removably and rotatably coupling the proximal and distal housings. In another exemplary embodiment, the proximal and distal housings can include threads for removably and rotatably coupling the proximal and distal housings to one another. The proximal and distal housings can have a threaded position, in which the threads are engaged for coupling the proximal and distal housings to one another, and an unthreaded position, in which the threads are not engaged and the proximal and distal housings are coupled together such that the proximal housing can freely rotate 360° relative to the distal housing. One of the proximal and distal housings can include at least one flange extending therefrom. The flange or flanges can be configured to engage at least one corresponding track formed in the other of the proximal and distal housings. The proximal housing can be configured to be removed from the distal housing when coupled thereto by moving the flange or flanges and the at least one corresponding track from being out of threaded engagement to being in threaded engagement and moving the proximal housing in a proximal direction relative to the distal housing. The at least one corresponding track can have an open distal terminal end such that when the proximal and distal housings are threaded together to couple the proximal and distal housings together, the open distal terminal end can allow the at least one flange to threadably disengage from and be positioned distal to the at least one corresponding track such that the proximal and distal housings are coupled together with the proximal housing configured to freely rotate 360° relative to the distal housing.

The surgical device can vary in any other number of ways. For example, a retractor can be mated to the distal housing and be configured to be positioned in an opening in tissue for forming a pathway through the tissue and into a body cavity.

In another embodiment, a surgical device is provided that includes a retractor and a housing removably coupled to the retractor. The retractor is configured to be positioned in an opening in tissue such that an instrument inserted into a working channel extending through the retractor can pass through the opening in the tissue and into a body cavity underlying the tissue. The housing includes a distal base removably coupled to the retractor, and a proximal cap removably coupled to the distal base and freely rotatable 360° relative to the distal base and the retractor. The housing also has a plurality of sealing ports in communication with the working channel in the retractor. Each of the sealing ports has a sealing element disposed therein.

The proximal cap can be can be removably coupled to the distal base in any way, such as by at least one living hinge formed on one of the proximal cap and the distal base or by a threaded engagement. In some embodiments, the proximal cap can be freely rotatable 360° clockwise and counterclockwise relative to the distal base and the retractor.

In another aspect, a surgical method is provided that includes positioning a retractor within an opening formed through tissue such that the retractor forms a working channel extending through the tissue and into a body cavity. The retractor is removably coupled to a housing having a sealing port including a sealing element. The method also includes inserting a surgical instrument through the sealing element and the working channel to position a distal end of the surgical instrument within the body cavity, and, with the distal end of the surgical instrument within the body cavity, moving the surgical instrument to cause at least a portion of the housing to rotate 360° relative to the retractor.

The method can have any number of variations. For example, the method can include releasably mating a proximal portion of the housing including the sealing port to a distal portion of the housing coupled to the retractor by engaging at least one mating element formed on one of the proximal and distal portions with at least one complementary mating feature formed on the other of the proximal and distal portions to releasably mate the proximal and distal portions such that proximal portion is freely rotatable 360° relative to the distal portion and the retractor. The proximal and distal portions can be releasably mated together in any number of ways. In one embodiment, the proximal portion can be aligned at any 360° rotational orientation relative to the distal portion, and the proximal and distal portions can be snapped together such that the proximal portion is freely rotatable 360° relative to the distal portion and the retractor. In another embodiment, the proximal and distal portions can be moved from a threaded position in which the proximal and distal portions are threadably engaged, to an unthreaded position in which the proximal and distal portions are not threadably engaged and the proximal portion is freely rotatable 360° relative to the distal portion and the retractor.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
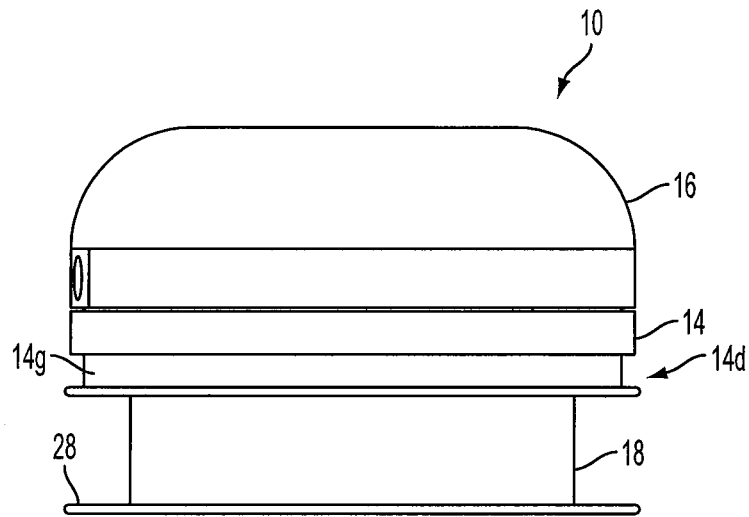
FIG. 1 is a side view of one embodiment of a surgical access device that includes a housing having releasably matable proximal and distal portions, and having a retractor coupled thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for accessing a body cavity. In general, the methods and devices allow one or more surgical instruments to be inserted through one or more independent access ports in a single surgical access device and delivered into a body cavity. The device can be configured to allow the instrument(s) to rotate about a central axis of the device, thus allowing for ease of manipulation within a patient's body. In one embodiment, a surgical access device includes a housing having at least one access port or sealing port for receiving a surgical instrument, and a retractor removably coupled to the housing and having a working channel configured to define a pathway through tissue and into a body cavity. Each sealing port can include one or more sealing elements therein for sealing the port and/or forming a seal around a surgical instrument disposed therethrough. The housing can include releasably matable upper and lower portions to allow for quick and easy assembly and disassembly of the housing, which can help save time during performance of a surgical procedure and/or can help provide fast, clear access to the retractor's working channel and the body cavity into which the retractor extends. A portion of the housing, e.g., the housing's upper portion, through which instruments can be inserted can be configured to rotate relative to a remainder of the housing, and to the retractor when the housing is mated thereto, thereby helping to optimally position the instrument(s) inserted therethrough and into the body cavity in which the retractor extends. In an exemplary embodiment, the housing's upper portion can freely rotate 360° relative to the remainder of the housing, and to the retractor when the housing is mated thereto.

As indicated above, the various surgical access devices can include a wound protector, cannula, or other member for forming a pathway through tissue, generally referred to as a "retractor". The retractor can extend from the housing and it can be configured to be positioned within an opening in a patient's body, such as the umbilicus. The sealing ports can each define working channels extending through the housing and aligned with the retractor. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitoneum, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

As surgical instruments are inserted through the surgical access device embodiments described herein, a risk can exist that a particularly sharp instrument may tear or puncture a portion of the retractor or nearby tissue. Accordingly, in any and all of the embodiments described herein, one or more retractor protectors or safety shields can optionally be positioned through, in, and around any of the components and/or tissue to reduce the risk of tearing or puncture by a surgical instrument inserted through the device. In general the retractor protector can be of a material that is relatively smooth and with a low coefficient of friction to allow ease of passage of instruments, but resistant to tearing and puncture. For example, the retractor protector can be formed of silicone, urethane, thermoplastic elastomer, rubber, polyolefins, polyesters, nylons, fluoropolymers, and any other suitable materials known in the art. The retractor protector can generally provide a liner for a retractor or tissue and can be fixed to or be detachable from a surgical access device. Exemplary embodiments of safety shields are described in more detail in U.S. patent application Ser. No. 12/399,625 filed Mar. 6, 2009 entitled "Methods And Devices For Providing Access Into A Body Cavity," U.S. application Ser. No. 12/399,482 filed Mar. 6, 2009 entitled "Methods and Devices for Providing Access to a Body Cavity," U.S. application Ser. No. 12/512,568 filed Jul. 30, 2009 entitled "Methods And Devices For Providing Access Into A Body Cavity," U.S. application Ser. No. 12/512,542 filed Jul. 30, 2009 entitled "Methods And Devices For Providing Access Into A Body Cavity," U.S. Patent Publication No. 2006/0247673 entitled "Multi-port Laparoscopic Access Device" filed Nov. 2, 2006, and U.S. application Ser. No. 12/242,765 entitled "Surgical Access Device" filed on Sep. 30, 2008, which are hereby incorporated by reference in their entireties.

In addition, as discussed further below, any and all embodiments of a surgical access device can include engagement and release components that allow certain components of the surgical access device to be removable as needed.

In use, and as also further discussed below, the surgical access devices disclosed herein can provide access to a patient's body cavity. The retractor can be positionable within an opening in a patient's body such that a distal portion of the retractor extends into a patient's body cavity and a proximal portion configured to couple to the housing is positioned adjacent to the patient's skin on an exterior of the patient's body. A lumen in the retractor can form a pathway through the opening in a patient's body so that surgical instruments can be inserted from outside the body to an interior body cavity. The elasticity of the skin of the patient can assist in the retention of the retractor in the body opening or incision made in the body. The retractor can be placed in any opening within a patient's body, whether a natural orifice or an opening made by an incision. In one embodiment, the retractor can be substantially flexible so that it can easily be maneuvered into and within tissue as needed. In other embodiments, the retractor can be substantially rigid or substantially semi-rigid. The retractor can be formed of any suitable material known in the art, e.g., silicone, urethane, thermoplastic elastomer, and rubber. Non-limiting examples of retractors include a Hakko® Wound Protector available from Hakko Medical Co. of Tokyo, Japan, an Alexis® Wound Protector available from Applied Medical Resources Corp. of Rancho Santa Margarita, Calif., and a Mobius® Retractor available from Apple Medical Corp. of Marlborough, Mass.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough, at least one channel seal or zero-closure seal that seals the working channel created by the sealing port when no instrument is disposed therethrough, or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment.

Figure 2:
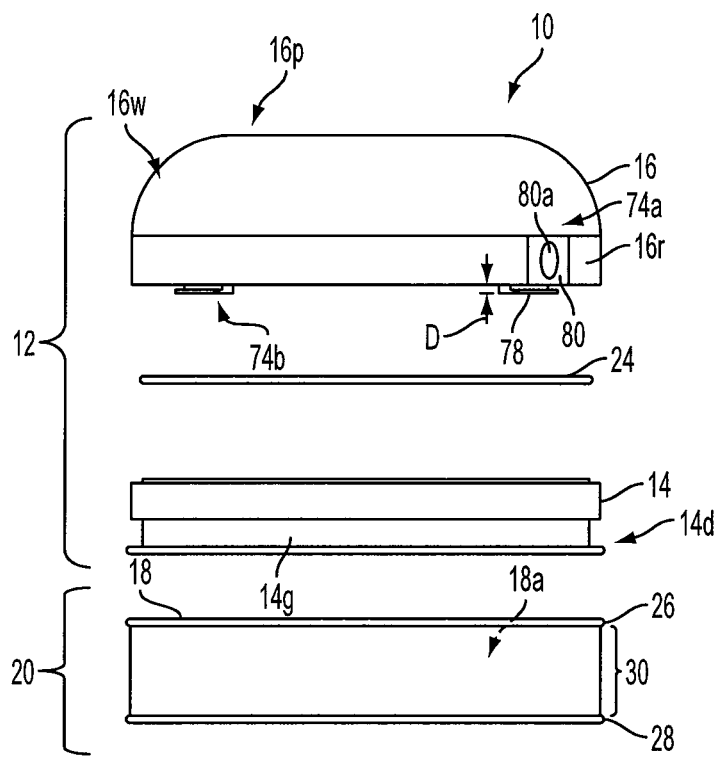
FIG. 2 is an exploded side view of the surgical access device of FIG. 1.
Figure 3:
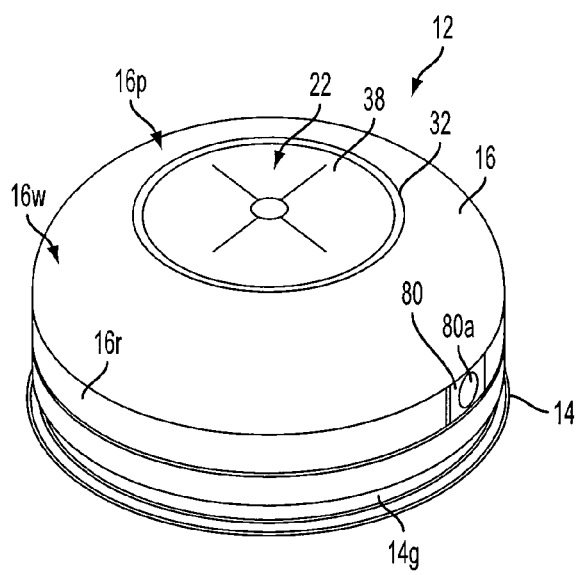
FIG. 3 is a perspective view of the housing of the surgical access device of FIG. 1.

In one exemplary embodiment, shown in FIGS. 1 and 2, a surgical access device 10 is provided having a proximal portion including a housing 12, and a distal portion 20 including a retractor 18 having an inner pathway, inner lumen, or working channel 18a extending therethrough. As shown in the illustrated embodiment, the housing 12 can be configured to have one or more surgical instruments inserted therethrough and can include a base, distal housing, or lower housing 14, generally referred to as a "distal housing," and a cap, proximal housing, or upper housing 16, generally referred to as a "proximal housing," that defines at least one sealing or access port. A sealing member, e.g., an o-ring 24, can be positioned between the distal and proximal housings 14, 16 to help form a fluid tight seal therebetween, as discussed further below. While the proximal housing 16 can define any number of sealing ports, in the illustrated embodiment, as shown in FIG. 3, the proximal housing 16 defines one sealing port 22 that extends through the proximal housing 16 and that seats a sealing element, as discussed further below. The proximal housing 16 can be configured to be removably coupled to the distal housing 14, which can be configured to be fixedly or removably mated to the retractor 18. In this way, at least a portion of the housing 12 can be configured to releasably mate to the retractor 18. The retractor 18 can thus be configured to distally extend from the housing 12 and to provide a pathway through tissue into a body cavity. The proximal housing 16 can be movable with respect to the distal housing 14 and the retractor 18, as will be discussed in more detail below. Such a configuration can help facilitate instrument positioning in a body cavity to which the device 10 provides access.

Although not shown in the illustrated embodiment, the device 10 can also include an insufflation port in the distal housing 14, although a person skilled in the art will appreciate that the insufflation port can be located elsewhere in the housing 12 or in other locations. A person skilled in the art will also appreciate that the insufflation port can have a variety of configurations. Generally, the insufflation port can be configured to pass an insufflation fluid through a flexible insufflation tube and into an insufflation orifice of the insufflation port where the fluid can flow between the distal housing 14 and the proximal housing 16, into the retractor's pathway 18a, and into a body cavity. A stopcock can control fluid flow through the insufflation tube. As described in more detail in previously mentioned U.S. application Ser. No. 12/512,568 filed Jul. 30, 2009 entitled "Methods And Devices For Providing Access Into A Body Cavity" and U.S. application Ser. No. 12/512,542 filed Jul. 30, 2009 entitled "Methods And Devices For Providing Access Into A Body Cavity," by having the insufflation port extend from the distal housing 14, the insufflation port can be configured to have a fixed rotational orientation relative to the retractor 18 regardless of the rotational orientation of the proximal housing 16 relative to the distal housing 14 and the retractor 18, thereby reducing chances of the insufflation tube twisting and/or becoming blocked or severed when the proximal housing 16 rotates. In this way, the insufflation port and the insufflation tube extending therefrom can be selectively positioned at a location less likely to cause interference with surgical instruments and/or surgical staff during a surgical procedure.

The housing 12 of the surgical access device 10 can have a variety of configurations. As shown in this embodiment, the proximal housing 16 can be in the form of a seal cap configured to releasably and rotatably mate to the distal housing 14, and the distal housing 14 can be in the form of a base ring configured to be disposed between the proximal housing 16 and the retractor 18 to form a seat and seal between the proximal housing 16 and the distal portion 20 of the device 10, e.g., the retractor 18. The distal housing 14, the proximal housing 16, the o-ring 24 configured to be positioned between the distal and proximal housings 14, 16, and the retractor 18 can each have various sizes, shapes, and configurations, as discussed further below.

As noted above, the retractor 18 can extend distally from a proximal portion of the device 10, e.g., the housing 12, and it can be configured to be positioned in an opening formed in tissue. As in the embodiment shown, the retractor 18 can be flexible and it can have a proximal flange 26 and a distal flange 28 with an inner elongate portion 30 extending therebetween. The inner elongate portion 30 of the retractor 18 can have a diameter less than a diameter of the proximal and distal flanges 26, 28, which can have the same diameter or different diameters from one another. The proximal flange 26 can be configured to be mated to a distal end 14d of the distal housing 14 in any way, such as by being seated within the distal housing 14. Alternatively, as shown in the embodiment illustrated in FIG. 1, the proximal flange 26 can be molded around the distal end 14d of the distal housing 14 and it can be seated in a circumferential groove 14g formed in and extending around a perimeter of an exterior or outer surface of the distal housing's distal end 14d. The retractor's proximal flange 26 can be optionally attached to the distal housing 14 using an adhesive, sealant, complementary threads, or any other attachment element, as will be appreciated by a person skilled in the art. A proximal o-ring can be optionally positioned within the proximal flange 26 and/or a distal o-ring can optionally be positioned within the distal flange 28 to help provide structural support to the retractor 18. The proximal and distal o-rings can be substantially flexible or substantially rigid, same or different from one another, as needed for use in a particular application. The retractor 18 can be molded as a cylindrical tube having a substantially constant diameter. The proximal and distal flanges 26, 28 can be formed by stretching proximal and distal ends of the cylindrical tube respectively around the proximal and distal o-rings to form the proximal and distal flanges 26, 28 having larger diameters than the inner elongate portion 30. A person skilled in the art will appreciate that the proximal and distal o-rings can be positioned in the proximal and distal flanges 26, 28 in any way, such as by stretching and folding ends of the molded retractor around the o-rings and bonding the edges around the o-rings.

The proximal housing 16 can also have a variety of sizes, shapes, and configurations, as can the sealing port 22 formed therein. As shown in FIG. 3, the sealing port 22 can be defined by a cut-out or opening 32 formed in the proximal housing 16. The opening 32 can extend through a proximal surface 16p of the proximal housing 16 such that it is exposed within an inner pathway, inner lumen, or working channel 14a defined by the distal housing 14. A person skilled in the art will appreciate that there can be any number of sealing ports formed in the proximal housing 16 that can be arranged in any way in the proximal housing 16. As in the illustrated embodiment, the sealing port 22 can have a central axis that extends substantially perpendicular to a plane of the proximal surface 16p of the proximal housing 16 and that is substantially parallel to a longitudinal axis of the retractor 18. The sealing port 22 can be in a fixed position relative to the proximal housing 16, as in the illustrated embodiment, but any one or more components in the sealing port 22 can be angled relative to the proximal housing 16 and/or be rotatable or otherwise movable relative to the proximal housing 16 and/or other portion(s) of the housing 12. The sealing port 22 in the illustrated embodiment is axially aligned with a central axis or center-point of the housing 12, e.g., a central axis or center-point of the proximal housing 16.

Figure 3A:
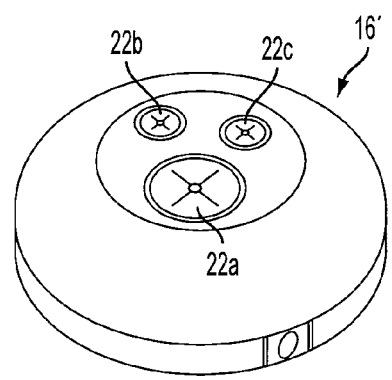
FIG. 3A is a perspective view of another embodiment of a proximal portion of a surgical access device housing that has multiple access ports.

FIG. 3A illustrates another exemplary embodiment of a proximal housing 16' that can be configured and used similar to the proximal housing 16, except the proximal housing 16' includes a plurality of sealing ports, namely first, second, and third ports 22a, 22b, 22c, that extend through the proximal housing 16' and that respectively seat first, second, and third sealing elements. The first, second, and third sealing ports 22a, 22b, 22c can be configured and used similar to the sealing port 22. In the illustrated embodiment, the multiple sealing ports 22a, 22b, 22c are radially arranged around a central axis or center-point of the proximal housing 16', e.g., a central axis or center-point of the proximal housing 16' as shown, such that each of the sealing ports 22a, 22b, 22c can have a central axis that differs from central axes of the other sealing ports 22a, 22b, 22c. Each of the sealing ports 22a, 22b, 22c can have central axes located any distance from the center point of the proximal housing 16'. In the illustrated embodiment, the second and third sealing ports 22b, 22c each have a diameter that is smaller than a diameter of the first sealing port 22a, but as mentioned above, the sealing ports 22a, 22b, 22c can have sizes same or different than any other of the sealing ports 22a, 22b, 22c. Exemplary embodiments of surgical access devices including multiple sealing ports are described in more detail in previously mentioned U.S. application Ser. No. 12/512,568 filed Jul. 30, 2009 entitled "Methods And Devices For Providing Access Into A Body Cavity," U.S. application Ser. No. 12/512,542 filed Jul. 30, 2009 entitled "Methods And Devices For Providing Access Into A Body Cavity," U.S. patent application Ser. No. 12/399,625 filed Mar. 6, 2009 entitled "Methods And Devices For Providing Access Into A Body Cavity," and U.S. application Ser. No. 12/399,482 filed Mar. 6, 2009 entitled "Methods and Devices for Providing Access to a Body Cavity."

Referring again to the embodiment illustrated in FIG. 3, the opening 32 in the proximal housing 16 can have any size and shape. In an exemplary embodiment, the opening 32 can have a diameter of less than about 16 mm to accommodate surgical instruments inserted therethrough having diameters less than about 16 mm. For non-limiting example, the housing 12 can have a diameter of about 75 mm, and the opening 32 can have a diameter in a range of about 6.0 to 7.5 mm, e.g., about 6.2 mm for receiving instruments having shaft diameters in a range of about 4.7 to 5.9 mm, or have a diameter of about 15.9 mm. As shown, the port opening 32 can have a shape corresponding to a shape of the sealing element seated therein, which in the illustrated embodiment is substantially circular. In embodiments having multiple sealing ports formed in the housing, any of the port openings can have shapes and sizes same or different than any other of the port openings.

The device 10 can optionally include at least one reducer cap (not shown) selectively and removably matable to the sealing port 22 to reduce a diameter thereof to allow a smaller surgical instrument to be inserted centrally therethrough while maintaining channel and instrument seals. In some embodiments, the reducer cap can be removably matable to a sealing element disposed in the sealing port 22 in addition to or instead of removably mating to the sealing port 22. Exemplary embodiments of reducer caps are described in more detail in previously mentioned U.S. patent application Ser. No. 12/399,625 filed Mar. 6, 2009 entitled "Methods And Devices For Providing Access Into A Body Cavity" and U.S. application Ser. No. 12/399,482 filed Mar. 6, 2009 entitled "Methods and Devices for Providing Access to a Body Cavity."

In some embodiments, the proximal surface 16p of the proximal housing 16 can be substantially flat with the port opening 32 by being formed in a same plane with each other, either co-planar parallel to the proximal surface 16p or recessed in the proximal housing 16. In some embodiments, the proximal surface 16p of the proximal housing 16 can be non-planar with at least one recessed portion extending in a plane distally displaced from and substantially parallel to a plane of the proximal surface 16p, and/or at least one raised portion proximally displaced from and substantially parallel to a plane of the proximal surface 16p. The proximal housing's one or more recessed portions and one or more raised portions can help compensate for sealing elements of different lengths to help prevent distal seal element openings of each of the sealing elements from contacting an interior of the retractor 18, at least when the surgical access device 10 is in an assembled configuration, e.g., as illustrated in FIG. 1, and at least when the device 10 is not positioned in tissue and has no surgical instruments inserted therethrough.

The device 10 can also include a seal base (not shown) having a cut-out or opening corresponding to and aligned with the opening 32 formed in the proximal housing 16 such that a surgical instrument can be inserted into the proximal housing opening 32 and the seal base opening and into the retractor 18, e.g., into the pathway 18a. Generally, the seal base can be configured to help secure a sealing element to the proximal housing 16 by securing the sealing element between the seal base and a distal surface of the proximal housing 16, as discussed further below. Exemplary embodiments of seal bases are described in more detail in previously mentioned U.S. application Ser. No. 12/512,568 filed Jul. 30, 2009 entitled "Methods And Devices For Providing Access Into A Body Cavity," U.S. application Ser. No. 12/512,542 filed Jul. 30, 2009 entitled "Methods And Devices For Providing Access Into A Body Cavity," U.S. patent application Ser. No. 12/399,625 filed Mar. 6, 2009 entitled "Methods And Devices For Providing Access Into A Body Cavity," and U.S. application Ser. No. 12/399,482 filed Mar. 6, 2009 entitled "Methods and Devices for Providing Access to a Body Cavity."

The sealing element disposed in the sealing port 22 can be attached or mated to the proximal housing 16 using any attachment or mating technique known in the art, but in the illustrated embodiment the sealing elements are engaged by an interference fit between the proximal housing 16 and the seal base. In general, the sealing port 22 can include an instrument seal and a channel or zero-closure seal disposed therein.

The sealing element can have a variety of sizes, shapes, and configurations. As shown in the illustrated embodiment in FIGS. 3 and 4, the sealing element includes a distal duckbill seal 34 that provides a channel seal, and a proximal septum seal 36 that provides an instrument seal. A protective member 38 can be positioned proximal to the septum seal 36 to protect the septum seal 36 from accidental puncture. The septum seal 36 can optionally include a beveled edge on an interior circumference thereof, which can help facilitate instrument insertion therethrough. If the septum seal 36 has an interior beveled edge, the protective member 38 can have an inner diameter substantially equal to an outer diameter of the beveled circumferential edge, which can help protect the septum seal 36 without floating in proximal or distal directions and without substantially limiting angular movement of instruments inserted therethrough. In use, when a surgical instrument is passed through the sealing port 22 through a center opening of the protective member 38 and the septum seal 36, the septum seal 36 can engage and form a seal around an outer surface of the instrument to thereby prevent the passage of fluids and gas through the seal. When no instrument is disposed therethrough, the center opening of the protective member 38 and the septum seal 36 will generally not form a seal in the working channel of the sealing port 22. Exemplary instrument seal configurations are described in more detail in U.S. Patent Publication No. 2004/0230161 entitled "Trocar Seal Assembly," filed on Mar. 31, 2004, and U.S. Patent Publication No. 2007/0185453 entitled "Conical Trocar Seal," filed on Oct. 15, 2003, which are hereby incorporated by reference in their entireties. When the instrument is further inserted through the duckbill seal 34, the instrument can open the duckbill seal 34 and pass into the working channel 18a of the retractor 18 when the retractor 18 is coupled to the housing 12. A person skilled in the art will appreciate that if the device 10 includes multiple sealing elements, any one or more of the sealing elements can be configured same or different from any of the other sealing elements.

Figure 4:
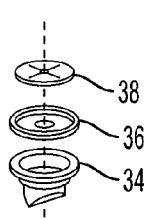
FIG. 4 is an exploded view of one embodiment of a sealing element.
Figure 5:
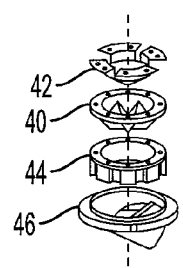
FIG. 5 is an exploded view of another embodiment of a sealing element.

In another exemplary embodiment of a sealing element shown in FIG. 5, the sealing element can include a fan seal 40, a fan seal protector 42 positioned concentric with and proximal to the fan seal 40, and a bottom ring 44 in which the fan seal 40 can be concentrically seated with the fan seal protector 42 to together form the instrument seal in the sealing port. A distal duckbill seal 46 can be positioned concentric and distal to the bottom ring 44. The duckbill seal 46 forms the channel or zero-closure seal to seal a working channel of the sealing port when no instrument is disposed therethrough to prevent leakage of insufflation gases delivered through the surgical access device to a body cavity. The duckbill seal 46 will generally not form a seal around an instrument inserted therethrough. The sealing port can generally be used in a manner similar to the sealing port 22 discussed above, with an instrument being insertable through a center opening in the fan seal protector 42 and the fan seal 40 and then through the duckbill seal 46 and into a working channel of the retractor 18 when the retractor 18 is coupled to the housing 12. The sealing elements illustrated in FIGS. 3-5 are described in more detail in previously mentioned U.S. application Ser. No. 12/512,568 filed Jul. 30, 2009 entitled "Methods And Devices For Providing Access Into A Body Cavity" and U.S. application Ser. No. 12/512,542 filed Jul. 30, 2009 entitled "Methods And Devices For Providing Access Into A Body Cavity."

Figure 6:
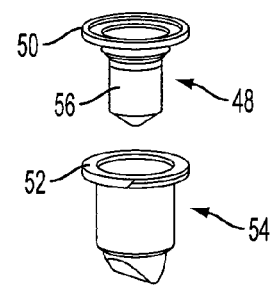
FIG. 6 is an exploded view of yet another embodiment of a sealing element.
Figure 7:
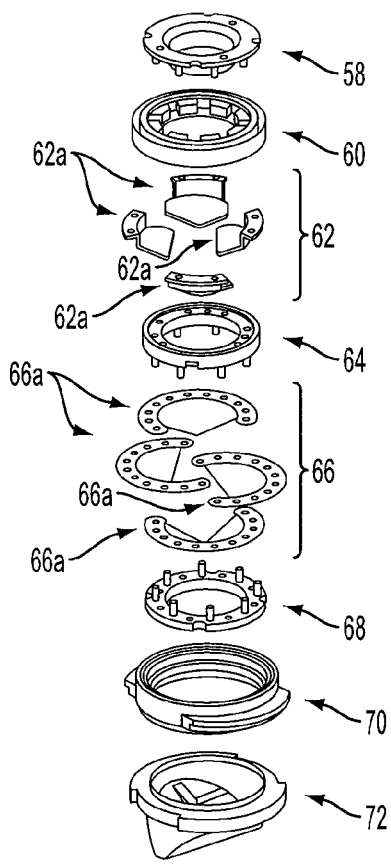
FIG. 7 is an exploded view of still another embodiment of a sealing element.

FIGS. 6 and 7 illustrate other exemplary embodiments of sealing elements. As shown in FIG. 6, a sealing element can include a deep cone seal 48 having a proximal flange 50 configured to seat on a proximal flange 52 of a distal duckbill seal 54 with a distal portion 56 of the deep cone 48 configured to be disposed within the distal duckbill seal 54. As shown in FIG. 7, another embodiment of a sealing element can include a crown 58, a washer 60, a multi-layer protective member 62 including a series of overlapping segments 62a configured as anti-eversion elements, a gasket ring 64, a multi-layer conical seal 66 including a series of overlapping seal segments 66a that are assembled in a woven arrangement to provide a complete seal body, a retainer ring 68, a spacer seal 70, and a distal duckbill seal 72. The sealing elements of FIGS. 6 and 7 are described in more detail in previously mentioned U.S. patent application Ser. No. 12/399,625 filed Mar. 6, 2009 entitled "Methods And Devices For Providing Access Into A Body Cavity" and U.S. application Ser. No. 12/399,482 filed Mar. 6, 2009 entitled "Methods and Devices for Providing Access to a Body Cavity."

Each of the distal duckbill seals 46, 34, 54, 72 and various other components of the various sealing elements can include a radially-outward extending proximal flange. The proximal flanges can each be captured between a proximal surface of the seal base and a distal surface of the proximal housing 16, thereby seating the sealing element within its associated port opening in the proximal housing 16. Whatever sealing element is seated in the proximal housing 16, the seal base and the proximal housing 16 can be sealingly engaged, thereby forming a seal around the sealing port 22. To seal together, one or more projections, e.g., cylindrical pegs or prongs, can proximally extend from a proximal surface of the seal base and each be inserted into a corresponding cavity, e.g., a cylindrical bore, formed in an inner or distal surface of the proximal housing 16.

A person skilled in the art will appreciate that while channel or zero-closure seals in the form of duckbill seals are shown for the distal seals 46, 34, 54, 72, any seal, e.g., duckbill seals, cone seals, flapper valves, gel seals, diaphragm seals, lip seals, iris seals, non-linear sealing elements such sealing elements with an S-shaped opening, etc., same or different from any other of the other distal seals 46, 34, 54, 72 can be used and can be aligned in any way relative to the proximal housing 16. Generally, a zero-closure seal can be configured to form a seal in a working channel when no instrument is disposed therethrough to thus prevent the leakage of insufflation gases delivered through the surgical access device to the body cavity. A duckbill seal can generally have opposed flaps that extend at an angle toward one another in a distal direction and that come together at a distal end to form a seal face. The opposed flaps can be movable relative to one another to allow the seal face to move between a closed position, in which no instrument is disposed therethrough and the seal face seals the working channel of the surgical access device, and an open position in which an instrument is disposed therethrough. A duckbill seal can include various other features, as described in more detail in U.S. Patent Publication No. 2009/0005799, entitled "Duckbill Seal with Fluid Drainage Feature," filed on Jun. 29, 2007, which is hereby incorporated by reference in its entirety. In addition, the seal face of the duckbill seal can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

As mentioned above, the sealing port 22 can be configured to be in a fixed position relative to the proximal housing 16, and to rotate with the proximal housing 16 relative to the distal housing 14 and the retractor 18, as discussed further below. However, the sealing port 22, and/or any one or more additional sealing ports of the proximal housing 16, can be configured to be movable relative to any one or more portions of the housing 12, such as the proximal housing 16, the distal housing 14, or any other sealing ports defined by the housing 12.

Regardless of the size, shape, and configuration of the one or more sealing elements seated in the proximal housing 16, as mentioned above, the proximal housing 16 can have a variety of sizes, shapes, and configurations, as can the distal housing 14. Referring again to FIGS. 1-3 as well as to FIGS. 8-10, the distal and proximal housings 14, 16 can each be configured as a substantially rigid cylindrical or circular member. Although the distal and proximal housings 14, 16 are each shown as a singular member, a person skilled in the art will appreciate that one or both of the distal and proximal housings 14, 16 can have multiple portions fixedly or removably mated together in any way, e.g., pins proximally extending from an outer perimeter of an upper portion can extend into corresponding bores formed in a circumferential wall of a lower portion to mate the upper and lower portions together.

As in the illustrated embodiment shown in FIGS. 1-3, 8, and 10, the proximal housing 16 can generally be configured as a domed cap and have a circumferential sidewall 16w extending distally from the proximal housing's proximal surface 16p. The proximal surface 16p and/or the circumferential sidewall 16w can optionally include one or more cut-out portions (not shown) formed therein adjacent to the sealing port 22 that are configured to help angle a surgical instrument inserted through the sealing port 22. For ease of illustration, no sealing element is shown seated in the proximal housing 16 in FIGS. 8 and 10. The proximal housing 16 can also include at least one mating element, e.g., first and second mating elements 74a, 74b in a distal rim 16r of the sidewall 16w, configured to facilitate coupling of the proximal housing 16 to the distal housing 14, as discussed further below.

The distal housing 14 can generally be configured as a ring defining the working channel 14a extending therethrough, as in the illustrated embodiment shown in FIGS. 1-3, 9, and 10. The distal housing's working channel 14a can be configured to align with the port opening 22 in the proximal housing 16 and with the pathway 18a in the retractor 18 such that an instrument inserted through the sealing element seated in the port opening 22 can pass through the pathways 14a, 18a and have at least its distal end extend distally beyond the device 10. The distal housing 14 can also include at least one mating feature, e.g., a circumferential groove or track 76, generally referred to as a "track," configured to facilitate coupling of the proximal housing 16 to the distal housing 14, as discussed further below. As in the illustrated embodiment, the circumferential track 76 can be formed in and continually extend 360° around a perimeter of an inner or interior surface 14s of the distal housing 14 in a proximal portion thereof.

As indicated above, when the distal and proximal housings 14, 16 are coupled together, e.g., as illustrated in FIGS. 1, 3, and 10-12, the o-ring 24 can be positioned therebetween to help provide a fluid tight seal between the distal and proximal housings 14, 16. In this way, the o-ring 24 can help prevent insufflation fluid from unintentionally escaping from the housing 12. Although the o-ring 24 can have a variety of sizes, shapes, and configurations, it can include an integral, single ring having a circular cross-sectional shape, as in the illustrated embodiment. Although the o-ring 24 is shown with a solid cross-section, it can have a hollow or partially hollow interior. The o-ring 24 can be flexible, rigid, or a combination thereof. A person skilled in the art will appreciate that although a fluid tight seal is provided in the illustrated embodiment using the o-ring 24, it can be provided between the distal and proximal housings 14, 16 when they are mated together in a variety of other ways.

Figure 13:
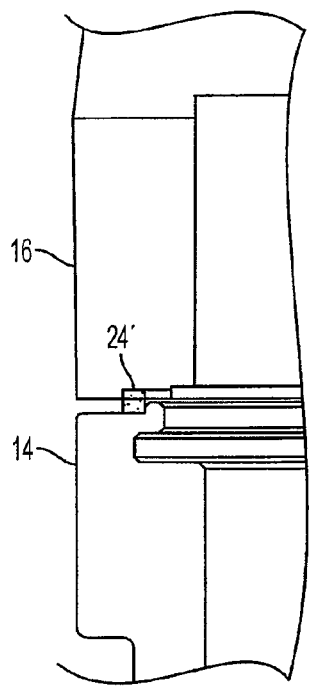
FIG. 13 is a side, partially cross-sectional view of another embodiment of a surgical access device housing that includes a foam ring positioned between releasably matable proximal and distal portions of the housing.

In another exemplary embodiment, a resilient ring can be positioned between the distal and proximal housings 14, 16 and it can be configured to be compressed therebetween when the distal and proximal housings 14, 16 are mated together. Generally, a resilient ring can be made from any flexible, composite material, e.g., a gel, a foam, an elastomer, isoplast (polyurethane), polyisoprene (natural rubber), santoprene (thermoplastic rubber), etc., configured to prevent fluid passage therethrough, to flex upon application of an external force without breaking, tearing, or otherwise allowing fluid to pass therethrough, and to dynamically flex to return to a default or resting position when the external force is removed. While a person skilled in the art will appreciate that any gel material can be used, a non-limiting example of a gel material includes a combination of an internal low molecular weight chemical species such as mineral oil or other oil, plasticizer, etc. and Kraton™ Rubber, e.g., styrene-ethylene/butylene-styrene (S-E/B-S) tri-block polymer, available from Kraton Polymers LLC of Houston, Tex. While a person skilled in the art will also appreciate that any foam material can be used, non-limiting examples of a foam material includes Kraton™ Rubber, silicone elastomers, polyurethanes, polyolefins such as polypropylene and polyethylene, polyolefin elastomers such as Santoprene™, e.g., a crosslinked co-polymer of polypropylene and EPDM (ethylene propylene diene M-class) rubber, available from Advanced Elastomer Systems, LP of Akron, Ohio, polyethylene-co-vinyl acetate copolymers, polytetrafluoroethylene (PTFE) in the form of expanded PTFE, etc. In one exemplary embodiment illustrated in FIG. 13, a resilient ring in the form of a foam ring 24' can be positioned between the distal and proximal housings 14, 16 and be configured to provide a fluid tight seal therebetween. Although the foam ring 24' can have a variety of sizes, shapes, and configurations, it can include an integral, single, circular ring as shown. The foam ring 24' has a square cross-sectional shape, although it can have any cross-sectional shape, e.g., z-shaped, circular-shaped, etc. The cross-sectional shape of the foam ring 24' can deform, as shown in FIG. 13, when the distal and proximal housings 14, 16 are mated together such that the foam ring 24' is compressed. Such deformation can help fill empty space between the distal and proximal housings 14, 16 and help prevent escape of fluid from between the distal and proximal housings 14, 16. As mentioned above, any resilient foam material can be used to form the foam ring 24', e.g., foamed polypropylene or polyethylene, sanoprene, and isoprene.

In any and all of the surgical access device embodiments disclosed herein, an engagement and/or release component can be included to allow, e.g., the proximal housing 16 to be attached to and separated from the distal housing 14, to allow the housing 12 to be separated from the retractor 18, and/or to allow a sealing element to be removed from the proximal housing 16. Any engagement and release component known in the art, e.g., a snap-lock mechanism, corresponding threads, etc., can be used to releasably mate two components of the device 10. When engaged, the distal and proximal housings 14, 16 form the housing 12 as a substantially rigid cylindrical or circular member with the proximal housing 16 rotatable relative to the distal housing 14, as discussed further below.

As illustrated in the embodiment shown in FIGS. 1-3 and 8-12, the device 10 can include an engagement and release component in the form of a living hinge configured to releasably couple the distal and proximal housings 14, 16. The first and second mating elements 74a, 74b of the proximal housing 16 can be configured to snap into and slide within the circumferential track 76 formed in the distal housing 14 to releasably couple the distal and proximal housings 14, 16. Although the proximal housing 16 can include any number of living hinges configured to slidably mate with the circumferential track 76, providing a plurality of radially arranged living hinges spaced equidistantly apart around a circumference of the proximal housing 16, as in the illustrated embodiment, can help stabilize the housing 12 and help facilitate smooth and free rotation of the proximal housing 16 relative to the distal housing 14. A person skilled in the art will appreciate that the first and second mating elements 74a, 74b can be spaced any distance apart around the distal housing's circumference. A person skilled in the art will also appreciate that in other embodiments the first and second mating elements 74a, 74b can be formed on the distal housing 14, and the circumferential track 76 can be formed in the proximal housing 16.

Figure 8:
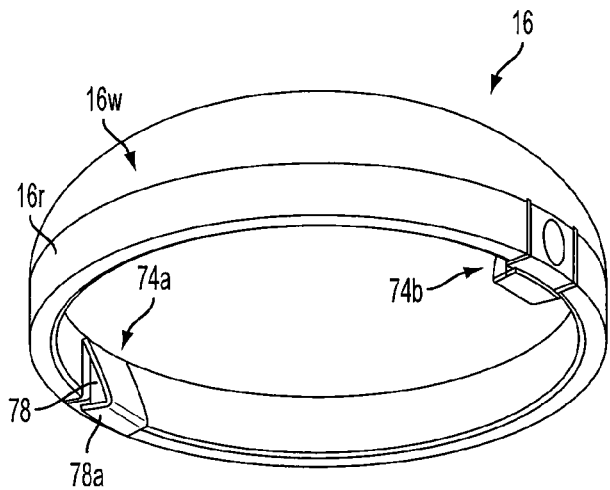
FIG. 8 is a perspective view of the proximal portion of the housing of FIG. 3.
Figure 9:
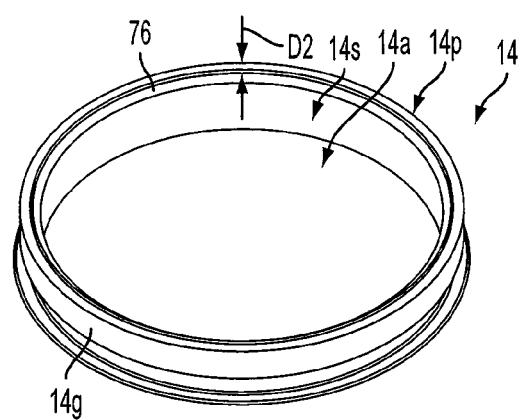
FIG. 9 is a perspective view of the distal portion of the housing of FIG. 3.
Figure 10:
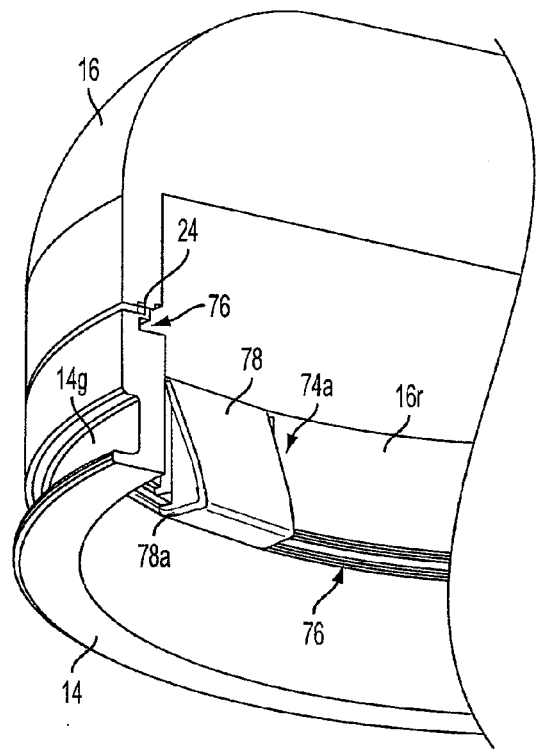
FIG. 10 is a perspective, partially cross-sectional view of the housing of FIG. 3.
Figure 11:
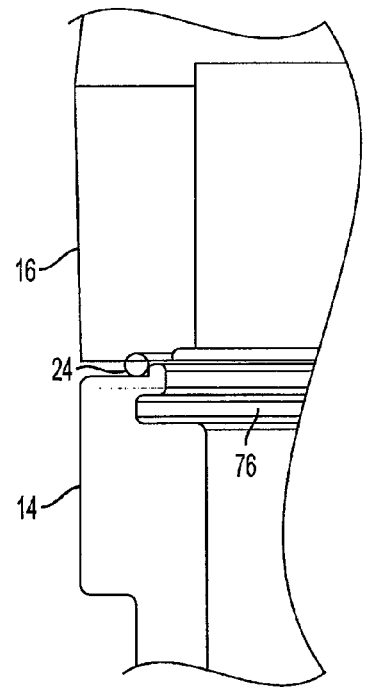
FIG. 11 is a side, partially cross-sectional view of the housing of FIG. 3.
Figure 12:
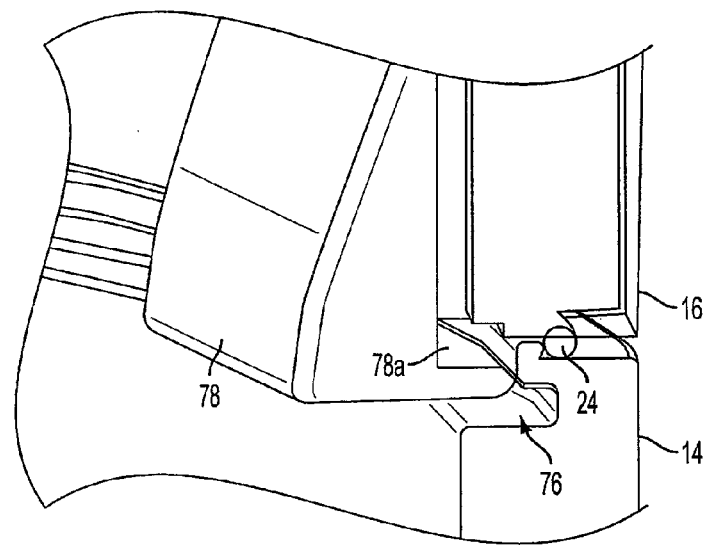
FIG. 12 is another perspective, partially cross-sectional view of the housing of FIG. 3.

The first and second mating elements 74a, 74b can have a variety of sizes, shapes, and configurations. Although the first and second mating elements 74a, 74b are identical in the illustrated embodiment, a person skilled in the art will appreciate that they can be the same or different from each another. For ease of explanation, only the first mating element 74a is described in more detail below. Generally, the first mating element 74a can have an engaged position for releasably and rotatably mating the distal housing 14 to the proximal housing 16, and can have a released position for allowing release of the proximal housing 16 from the distal housing 14. As shown in FIGS. 2, 8, 10, and 12, the first mating element 74a can be configured as a protrusion, flange, or foot, generally referred to as a "flange," that extends distally from the proximal housing 16 such that the flange can snap into the distal housing's circumferential track 76 and slide or move laterally therein when the proximal housing 16 rotates relative to the distal housing 14. The flange can be static, or it can be a movable member, e.g., hinge-like. The first mating element 74a can include an inner portion 78 and an outer portion 80 that cooperate together to allow the inner portion 78 to engage and release from the distal housing's circumferential track 76. The outer portion 80 can extend from an outer surface of the proximal housing 16, e.g., from an exterior surface of the proximal housing's sidewall 16w, as shown in FIGS. 2 and 3. The inner portion 78 can similarly extend from an inner surface of the proximal housing 16, e.g., from an interior surface of the proximal housing's sidewall 16w, as shown in FIGS. 8 and 10. The inner portion 78 of the first mating element 74a can extend a distance D distally beyond a remainder of the proximal housing 16, as shown in FIG. 2. This distance D can approximate a distance D2 that the circumferential track 76 is located from a proximal-most end 14p of the distal housing 14, as shown in FIG. 9. In this way, the distal extension of the first mating element 74a can help facilitate smooth and free rotation of the proximal housing 16 relative to the distal housing 14 by reducing, if not eliminating, direct contact of any other portion of the proximal housing 16 with the distal housing 14. As shown in FIGS. 8, 10, and 12, an inner surface of the inner portion 78 can have a protrusion 78a formed thereon, e.g., at a distal-most end thereof, that is configured to engage the circumferential track 76 of the distal housing 14. The protrusion 78a can have any size and shape, such as in the illustrated embodiment where the protrusion 78a is a bar extending radially-outward such that the inner portion 78 is L-shaped.

The circumferential track 76 can have a size and shape configured to receive the protrusion 78a. The circumferential track 76 can extend continuously 360° around the entire distal housing 14 such that when snapped therein, the inner portion 78 can be configured to continuously slide or move laterally therein to allow the proximal housing 16 to freely rotate 360° relative to the distal housing 14, selectively in both clockwise and counterclockwise directions. The proximal housing 16 being configured to be selectively rotated any amount in clockwise and counterclockwise directions can help more effectively position a surgical instrument inserted through the proximal housing 16 with respect to the surgical site and to other surgical tools simultaneously inserted through the device 10 or otherwise advanced to the surgical site. The circumferential track 76 can also be formed in the distal housing 14 at a constant axial position relative to a central longitudinal axis of the distal housing 14, e.g., be formed in a substantially level plane, such that when the distal and proximal housings 14, 16 are coupled together, the proximal housing 16 can rotate relative to the distal housing 14 in a level plane such that the proximal housing 16 does not substantially move proximally or distally relative to the distal housing 14.

Although the proximal housing 16 can be configured to be movable relative to the distal housing 14, and to the retractor 18 when the housing 12 is coupled thereto, with or without any instruments inserted through the sealing port 22, e.g., by being manually rotated by hand, the proximal housing 16 can also be configured to rotate relative to the distal housing 14, and the retractor 18, in response to motion of at least one instrument inserted through the port 22.

The first mating element 74a can be configured to automatically be in the engaged position, and it can be configured to be selectively movable from the engaged position to the released position by pressing and holding the outer portion 80, e.g., by pressing the outer portion 80 radially inwards, which can correspondingly move the inner portion 78, e.g., by pushing the inner portion 78 radially inward. The outer portion 80 can optionally include a gripping feature configured to facilitate depression of the outer portion 80 by a finger, a surgical instrument, and/or other tool. The gripping feature can have a variety of sizes, shapes, and configurations, e.g., a depression or indentation 80a formed therein (as shown in the illustrated embodiment in FIGS. 2 and 3), a textured surface, ridges, bumps, etc. At least a portion of the proximal housing 16, e.g., the sidewall 16w, can additionally or alternatively include a gripping feature to help facilitate manipulation thereof in coupling or decoupling the distal and proximal housings 14, 16 and in rotating the proximal housing 16 relative to the distal housing 14 when they are coupled together.

To couple the distal and proximal housings 14, 16 together, the proximal housing 16 can be snapped onto the distal housing 14, with the first and second mating elements 74a, 74b dynamically flexing as living hinges from the engaged position to the released position and back to the engaged position to engage the circumferential track 76 of the distal housing 14. The outer portion 80 can optionally be held pressed in when the distal and proximal housings 14, 16 are moved together to force the first mating element 74a into the released position. Then when the inner portion 78 is substantially aligned with the circumferential track 76, the outer portion 80 can be released to allow the inner portion 78 to move radially outward to the engaged position and engage the circumferential track 76. With the circumferential track 76 extending fully around the circumference of the distal housing 14 as in the illustrated embodiment, the proximal housing 16 can be coupled to the distal housing 14 at any 360° rotational orientation relative to the distal housing 14 with the first and second mating elements 74a, 74b snapping into the circumferential track 76 at any radial locations therearound. Similarly, the first and second mating elements 74a, 74b can disengage from the circumferential track 76 when the proximal housing 16 is at any 360° rotational orientation relative to the distal housing 14. Because the proximal housing 16 does not need to be aligned in any particular rotational orientation relative to the distal housing 14 when attached thereto or removed therefrom, the housing 12 can be quickly assembled and disassembled, which can be particularly beneficial given the time constraints of surgery. Before being attached to the proximal housing 16, the distal housing 14 can be pre-attached to the retractor 18, thereby allowing the device 10 to be fully assembled upon coupling of the proximal housing 16 to the distal housing 14.

The distal and proximal housings 14, 16 can be disengaged at any time before, during, or after surgery, e.g., to replace the proximal housing 16 with another proximal housing having a different number or different sizes of sealing ports or to have substantially unobstructed access to a body cavity underlying tissue in which the device 10 is positioned through the working channel 18a of the retractor 18 with or without the distal housing 14 remaining coupled to the retractor 18. If disengagement of the distal housing 14 and the proximal housing 16 is desired, the first and second mating elements 74a, 74b can be moved from the engaged position to the released position as discussed above such that the proximal housing 16 is free to be removed from the distal housing 14. With the first and second mating elements 74a, 74b disengaged from the circumferential track 76, e.g., in the released position, the proximal housing 16 can be moved proximally relative to the distal housing 14 to be removed therefrom. The first and second mating elements 74a, 74b can thus be configured as locks to selectively lock the proximal housing 16 to the distal housing 14 when the distal and proximal housings 14, 16 are coupled together. The distal and proximal housings 14, 16 can be in a locked configuration when the first and second mating elements 74a, 74b are in the engaged position with their inner portions positioned within the circumferential track 76, and the distal and proximal housings 14, 16 can be in an unlocked configuration when the first and second mating elements 74a, 74b are in the released position with their inner portions positioned outside the circumferential track 76. In this way, the proximal housing 16 can be configured to rotate relative to the distal housing 14 when coupled thereto in a locked configuration but otherwise not be movable relative to the distal housing 14 without first actuating the first and second mating elements 74a, 74b to move them from the engaged position to the released position such that the proximal housing 16 can be released from the distal housing 14. Such locking can help prevent the proximal housing 16 from being unintentionally released from the distal housing 14.

In use, one or more surgical instruments can be inserted into a body cavity through the surgical access device 10, which can help optimally position the surgical instruments relative to the body cavity through movement of the proximal housing 16 relative to the distal housing 14 and the retractor 18. The rotation of the proximal housing 16 can also help reduce the "chopstick" effect between surgical instruments present at the surgical site. The device 10 can be positioned within tissue to provide access to a body cavity underlying the tissue in a variety of ways. In one embodiment, the device 10 can be positioned in tissue fully assembled in the default position shown in FIG. 1. In another embodiment, the device 10 can be positioned partially assembled in tissue and be fully assembled with a portion of the device 10 positioned in the tissue. The various elements of the device 10 can be attached together in any order. In one embodiment, the device 10 can be positioned in tissue by first positioning the retractor 18 therein with the distal housing 14 being pre-attached to the retractor 18, and by then attaching the proximal housing 16 to the distal housing 14.

Figure 14:
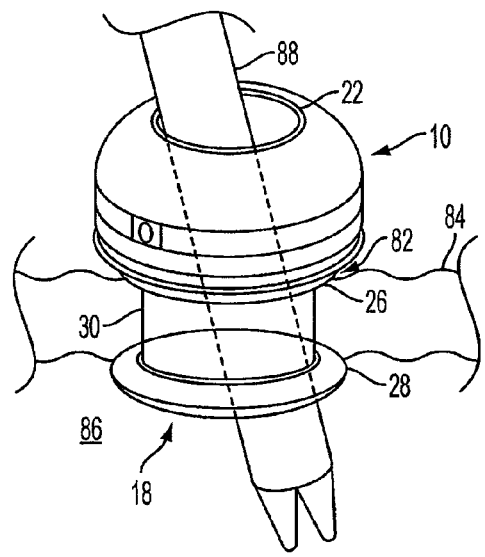
FIG. 14 is a side, partially cross-sectional view of the surgical access device of FIG. 1 positioned in an opening formed in tissue and having a surgical instrument inserted therethrough.

In one embodiment, illustrated in FIG. 14, the retractor 18 can be positioned within an opening or incision 82, generally referred to as an "opening," formed in tissue 84, e.g., in the umbilicus, with the proximal and distal flanges 26, 28 of the retractor 18 positioned on opposed sides of the tissue 84. The opening 82 can have any shape and size, e.g., a linear cut having a longitudinal length in a range of about 15 to 35 mm and extending through a layer of tissue having a depth of less than about 70 mm. The distal housing 14 coupled to a proximal portion of the retractor 18 can be positioned on one side of the tissue 84, as can the housing 12 when fully assembled, with the retractor 18 extending through the tissue opening 82 and into a body cavity 86 underlying the tissue 84. The distal flange 28 of the retractor 18 can be positioned on and/or distal to a distal surface of the tissue 84 in the body cavity 86. The inner elongate portion 30 of the retractor 18 can thereby be positioned within the tissue 84 with the working channel 18a of the retractor 18 extending through the tissue 84 to provide a path of access to the body cavity 86. The retractor 18 can be positioned within the tissue opening 82 in any way, as will be appreciated by a person skilled in the art. Exemplary devices and methods for positioning the retractor 18 in the tissue opening 82 by hand and by using an inserter tool are described in more detail in previously mentioned U.S. application Ser. No. 12/512,568 filed Jul. 30, 2009 entitled "Methods And Devices For Providing Access Into A Body Cavity" and U.S. application Ser. No. 12/512,542 filed Jul. 30, 2009 entitled "Methods And Devices For Providing Access Into A Body Cavity."

With the retractor 18 positioned in the tissue 84, the housing 12 can be attached to the retractor 18 to fully assemble the device 10. If the tissue 84 and/or the retractor 18 are adequately flexible, the retractor 18 can be angled or pivoted to a desired position to ease attachment of the housing 12 and the retractor 18. The retractor 18 can also be angled or pivoted during use of the device 10 with one or more surgical instruments inserted therethrough. As mentioned above, in an exemplary embodiment, the retractor 18 with the distal housing 14 coupled thereto is positioned within the tissue opening 82, and then the proximal housing 16 is coupled to the distal housing 14 and the retractor 18 such that the housing 12 is coupled to the retractor 18. As also mentioned above, the proximal housing 16 can be mated to the distal housing 14 and the retractor 18 by snapping the proximal housing's first and second mating elements 74a, 74b into the circumferential track 76 of the distal housing 14. The tissue 84 can provide adequate tension such that the distal housing 14 and the retractor 18 need not be held in position while the proximal housing 16 is attached or rotated relative thereto, although the distal housing 14 and/or the retractor 18 can be so held to help provide support to the device 10.

With the surgical access device 10 assembled and positioned in the tissue 84, a surgical instrument 88 can be inserted through the sealing port 22 and into the body cavity 86 where the instrument 88 can help perform any type of surgical procedure. Prior to insertion of the instrument 88 through the device 10, insufflation can be provided using an insufflation port, tubing, and a stopcock as discussed above. Although the surgical instrument 88 shown in FIG. 14 is a grasper having a pair of distal movable jaws, a person skilled in the art will appreciate that any surgical instrument can be inserted through the device 10. Further, although the illustrated device 10 includes one sealing port 22, as mentioned above, the device 10 can include multiple sealing ports configured to each simultaneously have an instrument inserted therethrough.

At any point before, during, or after a surgical procedure, the device 10 can be removed from the tissue 84. Moreover, at any point before, during, or after a surgical procedure, the housing 12 in full or in part, e.g., only the proximal housing 16, can be released from the retractor 18, and the retractor 18 and any portion of the device 10 attached thereto can be removed from the tissue 84. To disengage the proximal housing 16 from the distal housing 14 and the retractor 18, the proximal housing 16 can be moved proximally relative to the distal housing 14 and the retractor 18. As mentioned above, the engagement and release component can be disengaged to allow the proximal housing 16 to be proximally moved relative to the distal housing 14 and the retractor 18, e.g., the outer portions of the first and second mating elements 74a, 74b can be depressed to push in their respective inner portions. The tissue 84 can provide adequate tension for the proximal motion of the proximal housing 16.

With the housing 12 disengaged in full or in part from the retractor 18, the working channel 18a of the retractor 18 can provide access to the body cavity 86 underlying the tissue 84. With or without the distal housing 14 also removed from the retractor 18, one or more surgical instruments can be advanced through the retractor's working channel 18a, such as a waste removal bag configured to hold waste material, e.g., dissected tissue, excess fluid, etc., from the body cavity 86. The bag can be introduced into the body cavity 86 through the retractor's working channel 18a or other access port. A person skilled in the art will appreciate that one or more surgical instruments can be advanced through the retractor's working channel 18a before and/or after the proximal housing 16 and/or the distal housing 14 has been attached to the retractor 18.

The retractor 18 can be removed from within the tissue opening 82 in any way. In some embodiments, the retractor 18 can be pulled out of the opening 82 by hand, e.g., by inserting a finger through the retractor's inner lumen 18a and pulling the distal flange 28 from the body cavity 86 through the proximal flange 26. In some embodiments, a string, thread, suture, or cord (not shown), generally referred to as a "cord", can be used to help remove the retractor 18 from the tissue 84, with or without the proximal housing 16 and/or the distal housing 14 being attached to the retractor 18. The cord can have a variety of sizes, shapes, and configurations. Generally, the cord can be a surgically safe flexible material, such as umbilical tape. Exemplary embodiments of a cord are described in more detail in previously mentioned U.S. application Ser. No. 12/512,568 filed Jul. 30, 2009 entitled "Methods And Devices For Providing Access Into A Body Cavity" and U.S. application Ser. No. 12/512,542 filed Jul. 30, 2009 entitled "Methods And Devices For Providing Access Into A Body Cavity." A surgical drape can optionally be placed over the retractor 18 and the tissue opening 82 during removal of the retractor 18 to help reduce dispersion of bodily fluid outside the surgical space.

Figure 15:
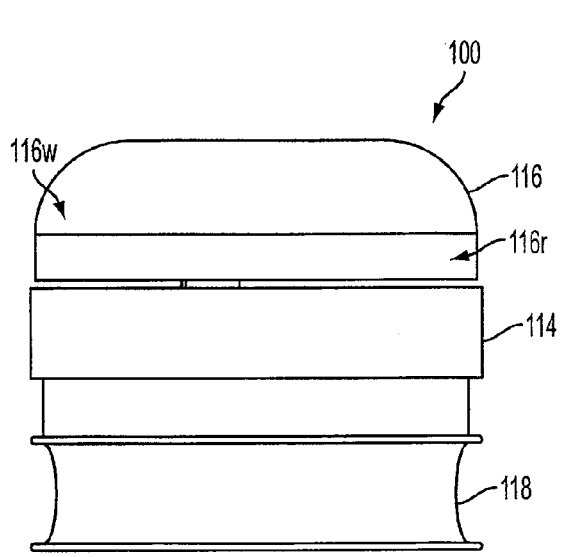
FIG. 15 is a side view of another embodiment of a surgical access device that includes a housing having releasably matable proximal and distal portions, and having a retractor coupled thereto.
Figure 16:
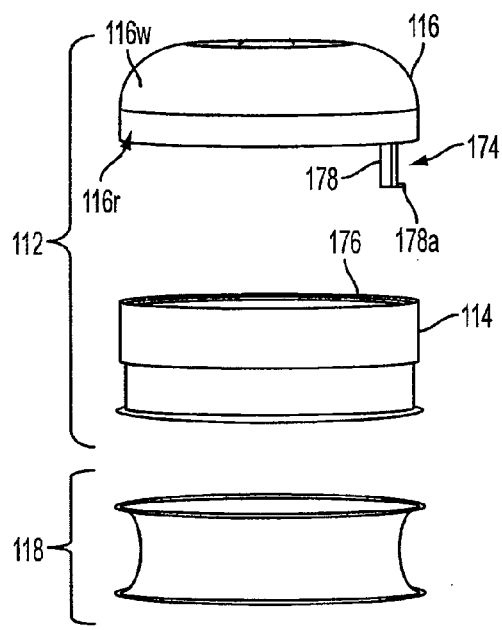
FIG. 16 is an exploded side view of the surgical access device of FIG. 15.
Figure 17:
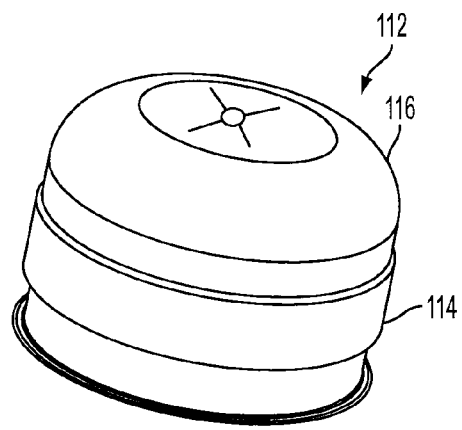
FIG. 17 is a perspective view of the housing of the surgical access device of FIG. 15.

FIGS. 15 and 16 illustrate another exemplary embodiment of a surgical access device 100 that includes a proximal housing 116 configured to removably and rotatably couple with a distal housing 114 and freely and selectively rotate 360° clockwise and counterclockwise relative thereto. The surgical access device 100 can be configured and used similar to the surgical access device 10 of FIG. 1 discussed above. However, a housing 112 in this embodiment, also shown in FIGS. 17 and 18, including the distal and proximal housings 114, 116 has an engagement and release component in the form of a thread configured to releasably mate the distal and proximal housings 114, 116 while allowing non-threaded rotational movement of the proximal housing 116 relative to the distal housing 114, and to a retractor 118 when the assembled housing 112 is coupled thereto. Although not shown in the illustrated embodiment, a sealing member can be positioned between the distal and proximal housings 114, 116 to help provide a fluid tight seal therebetween when they are coupled together.

The thread can generally include complementary threadable members formed on the distal and proximal housings 114, 116. As shown in FIGS. 16 and 18-20, the proximal housing 116 can include at least one mating element, e.g., a bayonet foot, flange, or pin 174, configured to facilitate coupling of the proximal housing 116 to the distal housing 114 in cooperation with at least one mating feature, e.g., a tapering circumferential track 176, of the distal housing 114. A person skilled in the art will appreciate that in other embodiments foot 174 can be formed on the distal housing 114, and the tapering circumferential track 176 can be formed in the proximal housing 116.

The foot 174 and the tapering circumferential track 176 can each have a variety of sizes, shapes, and configurations. As in the illustrated embodiment, shown in FIGS. 16, 18, and 19, the foot 174 can extend distally from a sidewall 116w of the proximal housing 116, e.g., from a distal rim 116r thereof, and be configured to engage the circumferential track 176 and slide or thread therein to couple the distal and proximal housings 114, 116. The foot 174 can extend distally from an inner surface of the proximal housing's sidewall 116w with a protrusion 178a formed thereon, e.g., at a distal-most end thereof. The protrusion 178a can be configured to engage and move within the tapering circumferential track 176 of the distal housing 114. The protrusion 178a can have any size and shape, such as a radially-outward extending bar, as shown. The tapering circumferential track 176 can have a size and shape configured to receive the protrusion 178a. As also shown in the illustrated embodiment in FIGS. 18 and 20, the tapering circumferential track 176 can be formed in and around a perimeter of an inner or interior surface 114s of the distal housing 114 in a proximal portion thereof. The tapering circumferential track 176 can continually extend 360° around the distal housing 114 as in the illustrated embodiment, or it can extend less than 360° around the distal housing 114. The tapering circumferential track 176 can also be formed in the distal housing 114 at a variable axial position, e.g., be tapering, relative to a central longitudinal axis of the distal housing 114, with the track's proximal terminal end 176p being located proximal to the track's distal terminal end 176b, thereby allowing the foot 174 to disengage from the track 176, as discussed further below.

Figure 18:
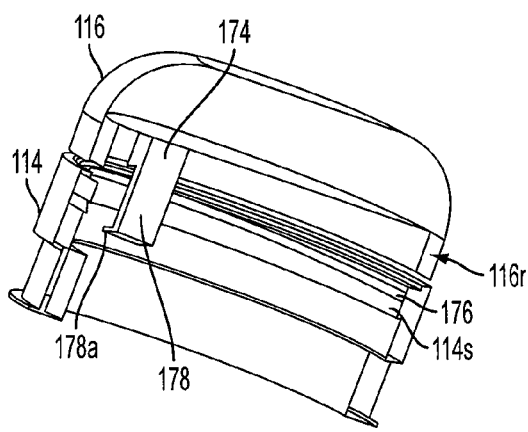
FIG. 18 is a perspective cross-sectional view of the housing of FIG. 17.
Figure 19:
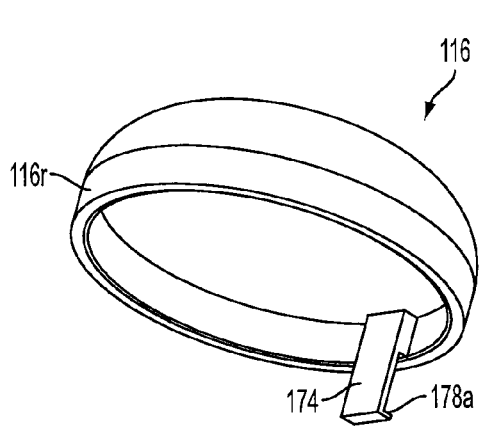
FIG. 19 is a perspective view of the proximal portion of the housing of FIG. 17.
Figure 20:
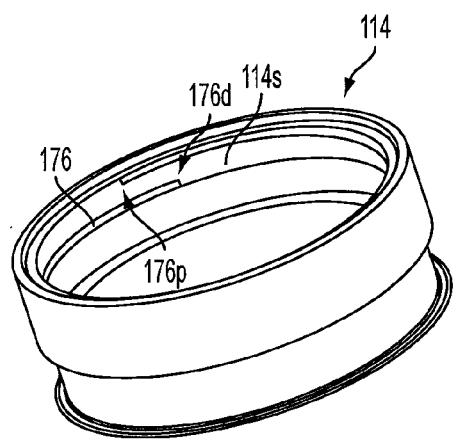
FIG. 20 is a perspective view of the distal portion of the housing of FIG. 17.

Generally, the foot 174 can be configured to have a threaded position in which the foot 174 threadably engages the tapering circumferential track 176 and can slide therein until the proximal housing 116 is rotated a threshold distance relative to the distal housing 114, at which point the foot 174 and the tapering circumferential track 176 are released from threaded engagement. To attach the proximal housing 116 to the distal housing 114, the foot 174 can enter the tapering circumferential track 176 at an open or threadless proximal end 176p, generally referred to as an "open proximal end," thereof and can be released from threaded engagement by sliding out of an open or threadless distal end 176d, generally referred to as an "open proximal end," of the tapering circumferential track 176 and drop to a position distal to the tapering circumferential track 176 within a working channel 114a of the distal housing 114, as shown in FIG. 18, and/or within a working channel 118a of the retractor 118 when the housing 112 is coupled to the retractor 118. The threshold distance corresponds to a length of the tapering circumferential track 176 around the distal housing's perimeter, e.g., the length between the track's proximal and distal ends 176p, 176d. The foot 174 can thus have a threaded position for coupling the proximal housing 116 to the distal housing 114 in which the foot 174 is engaged with the tapering circumferential track 176 and an unthreaded position with the foot 174 out of engagement with the track 176 and being positioned distal to the tapering circumferential track 176. With the foot 174 in the unthreaded position, the proximal and distal housings 116, 114 can be coupled together with the proximal housing 116 being selectively and freely rotatable relative to the distal housing 114 360° clockwise and counterclockwise without the distal and proximal housings 114, 116 being in threaded engagement. Moreover, with the foot 174 in the unthreaded position, e.g., positioned below the track 176, the proximal housing 116 can be configured to freely rotate relative to the distal housing 114 to be positioned at any 360° rotational orientation relative thereto without the proximal housing 116 being releasable from the distal housing 114 and at risk of being unintentionally unattached therefrom. In other words, with the foot 174 in the unthreaded position, rotating the proximal housing 116 relative to the distal housing 114 will not remove it from the distal housing 114.

If disengagement of the distal housing 114 and the proximal housing 116 is desired, the foot 174 can be moved from the unthreaded position into the threaded position by moving the proximal housing 116 in a proximal direction relative to the distal housing 114 and moving the protrusion 178a of the foot 174 into the track 176 through the track's open distal end 176d and threadably rotating the proximal housing 116 relative to the distal housing 114 until the foot 174 exits the track 176 at the track's proximal end 176p.

Although the proximal housing 116 in the illustrated embodiment includes only one foot 174 and the distal housing 114 includes only one tapering circumferential track 176, the housing 112 can include any number of feet and any number of tapering circumferential tracks. In one exemplary embodiment, a proximal housing can include a plurality of bayonet feet, flanges, or pins, and a distal housing can include a same number of tapering circumferential tracks. Each of the feet can be configured to slidably engage one of the tapering circumferential tracks and slide therein until released from a distal end thereof and being positioned distal thereto. The multiple feet can have any shape and size and can be the same as or different from any other of the feet. The multiple feet can be configured to be identical and interchangeably lowered into any of the multiple tracks in the distal housing. Alternatively, any one or more of the feet can differ from one another in size and/or shape, and one or more of the tracks can correspondingly differ, such that the distal housing can be configured to mate to the proximal housing in one or more predetermined rotational orientations, e.g., with different circumferentially arranged feet aligned with their corresponding different circumferentially arranged tracks. In an embodiment where each of the feet differs from one another and each of the tracks correspondingly differs from one another, the proximal housing can only be positioned in one predetermined rotational orientation relative to the distal housing where the feet can each be simultaneously engaged with their corresponding tracks. Various embodiments of differing bayonet feet are described in more detail in previously mentioned U.S. application Ser. No. 12/399,482 entitled "Methods and Devices for Providing Access to a Body Cavity" filed on Mar. 6, 2009.

As will be appreciated by those skilled in the art, any and all of the embodiments disclosed herein can be interchangeable with one another as needed. For example, an exemplary surgical access device kit could include multiple housings with one or more retractors. Each housing can have different sealing port configurations including different types and numbers of sealing elements, etc. as needed in particular application. Various release components known in the art can be used to releasably attach the various housings to a retractor.

There are various features that can optionally be included with any and all of the surgical access device embodiments disclosed herein. For example, a component of the device, such as a proximal housing, distal housing, retractor, sealing element, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. Publication No. 2010/0081863 entitled "Methods and Devices for Performing Gastrectomies and Gastroplasties" filed on Sep. 30, 2008; U.S. Publication No. 2010/0081864 entitled "Methods and Devices for Performing Gastrectomies and Gastroplasties" filed on Sep. 30, 2008; and U.S. application Ser. No.

12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a proximal housing, a sealing element, a retractor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a refractor configured to be positioned in an opening in tissue such that an instrument inserted into a working channel extending through the retractor can pass through the opening in the tissue and into a body cavity underlying the tissue; and
a housing removably coupled to the retractor and having a plurality of sealing ports in communication with the working channel in the retractor, each of the sealing ports having a sealing element disposed therein, the housing including a distal base removably coupled to the retractor, and a proximal cap removably coupled to the distal base so as to form a fluid tight seal, the proximal cap being freely rotatable 360° relative to the distal base and the retractor when the proximal cap is removably coupled to the distal base.

2. The device of claim 1, wherein when the proximal cap is removably coupled to the distal base, the proximal cap is freely rotatable 360° clockwise and counterclockwise relative to the distal base and the retractor.

3. The device of claim 1, wherein the proximal cap is removably coupled to the distal base by at least one living hinge formed on one of the proximal cap and the distal base.

4. The device of claim 3, wherein the at least one living hinge is formed on an internal surface of the one of the proximal cap and the distal base and extends radially inward from the internal surface.

5. The device of claim 3, wherein one of the proximal cap and the distal base has a track formed therein, the at least one living hinge being configured to move within the track when the proximal cap is freely rotated 360° relative to the distal base and the retractor when the proximal cap is removably coupled to the distal base.

6. The device of claim 5, wherein the at least one living hinge is formed on an internal surface of the one of the proximal cap and the distal base, and the track is formed in an internal surface of another of the proximal cap and the distal base.

7. The device of claim 1, wherein the proximal cap is removably coupled to the distal base by a threaded engagement.

8. The device of claim 1, wherein when the proximal cap is removably coupled to the distal base, the sealing ports as a unit are freely rotatable 360° relative to the distal base and the retractor.

9. The device of claim 1, further comprising a sealing member positioned between the distal base and the proximal cap when the distal base is removably coupled to the retractor and the proximal cap is removably coupled to the distal base, the sealing member providing the fluid tight seal.

10. The device of claim 9, wherein the sealing member comprises an o-ring.

11. The device of claim 1, wherein the proximal cap includes a mating element, and the distal base includes a mating feature, the mating element being selectively releasable from the mating feature so as to remove the proximal cap from the distal base, and the mating element being selectively attachable to the mating feature so as to removably couple the proximal cap to the distal base.

12. A surgical device, comprising:
a refractor configured to be positioned in an opening in tissue such that an instrument inserted into a working channel extending through the retractor can pass through the opening in the tissue and into a body cavity underlying the tissue; and
a housing configured to removably couple to the retractor, the housing having a plurality of sealing ports in communication with the working channel in the refractor, each of the sealing ports having a sealing element disposed therein, the housing including a distal base and a proximal cap, the distal base being configured to removably couple to the retractor and including a mating feature, and the proximal cap being configured to removably couple to the distal base and including a mating element configured to releasably mate to the mating feature, wherein when the mating feature is mated to the mating element, the proximal cap is releasably fixed to the distal base and the proximal cap is freely rotatable 360° relative to the distal base and the refractor.

13. The device of claim 12, wherein a fluid tight seal is formed between the proximal cap and the distal base when the proximal cap and the distal base are removably coupled together such that the proximal cap can freely rotate 360° relative to the distal base without release of the fluid tight seal.

14. The device of claim 12, wherein when the mating feature is mated to the mating element, the proximal cap is freely rotatable 360° clockwise and counterclockwise relative to the distal base and the retractor.

15. The device of claim 12, wherein when the mating feature is mated to the mating element, the proximal cap is configured to be released from the distal base by disengagement of the mating feature and the mating element.

16. The device of claim 12, wherein when the mating feature is mated to the mating element, the proximal cap is freely rotatable 360° relative to the distal base in a substantially fixed plane substantially perpendicular to a longitudinal axis of the working channel.

17. The device of claim 12, wherein at least one of the mating element and the mating feature comprises at least one living hinge.

18. The device of claim 12, wherein the mating feature and the mating element comprises complementary threads such that the proximal cap is configured to removably couple to the distal base by a threaded engagement.

* * * * *